(12) United States Patent
Hancock et al.

(10) Patent No.: US 7,897,741 B2
(45) Date of Patent: Mar. 1, 2011

(54) CELL CYCLE PHASE MARKERS

(75) Inventors: Suzanne Hancock, Cardiff (GB); Simon Stubbs, Cardiff (GB); Nicholas Thomas, Cardiff (GB); Ellen Fanning, Nashville, TN (US); Jinming Gu, Boston, MA (US)

(73) Assignee: GE Healthcare UK Limited, Amersham (GB)

( * ) Notice: Subject to any disclaimer, the term of this patent is extended or adjusted under 35 U.S.C. 154(b) by 0 days.

(21) Appl. No.: 12/560,519

(22) Filed: Sep. 16, 2009

(65) Prior Publication Data

US 2010/0028899 A1    Feb. 4, 2010

Related U.S. Application Data

(62) Division of application No. 11/572,510, filed as application No. PCT/GB2005/002884 on Jul. 22, 2005, now Pat. No. 7,612,189.

(60) Provisional application No. 60/590,814, filed on Jul. 23, 2004, provisional application No. 60/645,915, filed on Jan. 21, 2005, provisional application No. 60/645,968, filed on Jan. 21, 2005.

(51) Int. Cl.
*C07H 21/02* (2006.01)
(52) U.S. Cl. .................................... 536/23.1
(58) Field of Classification Search ....................... None
See application file for complete search history.

(56) References Cited

PUBLICATIONS

Gu et al (Molecular Biology of the Cell, Jul. 2004, 15:3320-3332).*
Kakinoki et al (JBC, Dec. 1997, 272(51): 32308-32314).*
Taneja et al (JBC, Oct. 2002, 277(43): 40853-40861).*
Ivic et al (J Neurobiol, 2002, 50(1): 56-68).*

* cited by examiner

*Primary Examiner*—Sean E Aeder
(74) *Attorney, Agent, or Firm*—Yonggang Ji

(57) ABSTRACT

The present invention relates to polypeptide and nucleic acids constructs which are useful for determining the cell cycle status of a mammalian cell. Host cells transfected with these nucleic acid constructs can be used to determine the effects that test agents have upon the mammalian cell cycle.

17 Claims, 12 Drawing Sheets

CELL CYCLE PHASE MARKERS

CROSS REFERENCE TO RELATED APPLICATIONS

This application is a divisional of U.S. patent application Ser. No. 11/572,510 filed Jan. 23, 2007, now U.S. Pat. No. 7,612,189, which is a filing under 35 U.S.C. §371 and claims priority to international patent application number PCT/GB2005/002884 filed Jul. 22, 2005, published on Jan. 26, 2006, as WO 2006/008542, which claims priority to U.S. provisional patent application Nos. 60/590,814 filed Jul. 23, 2004, 60/645,915 filed Jan. 21, 2005 and 60/645,968 filed Jan. 21, 2005.

GOVERNMENT SUPPORT

This invention was made with government support under GM052948 awarded by the NIH. The government has certain rights in the invention.

TECHNICAL FIELD

The present invention relates to cell cycle phase-specific markers and methods for determining the transition between different phases of the cell cycle in mammalian cells.

BACKGROUND OF THE INVENTION

Eukaryotic cell division proceeds through a highly regulated cell cycle comprising consecutive phases termed G1, S, G2 and M. Disruption of the cell cycle or cell cycle control can result in cellular abnormalities or disease states such as cancer which arise from multiple genetic changes that transform growth-limited cells into highly invasive cells that are unresponsive to normal control of growth. Transition of normal cells into cancer cells can arise though loss of correct function in DNA replication and DNA repair mechanisms. All dividing cells are subject to a number of control mechanisms, known as cell-cycle checkpoints, which maintain genomic integrity by arresting or inducing destruction of aberrant cells. Investigation of cell cycle progression and control is consequently of significant interest in designing anticancer drugs (Flatt, P. M. and Pietenpol, J. A. Drug Metab. Rev., (2000), 32(3-4), 283-305; Buolamwini, J. K. Current Pharmaceutical Design, (2000), 6, 379-392).

Cell cycle progression is tightly regulated by defined temporal and spatial expression, localisation and destruction of a number of cell cycle regulators which exhibit highly dynamic behaviour during the cell cycle (Pines, J., Nature Cell Biology, (1999), 1, E73-E79). For example, at specific cell cycle stages some proteins translocate from the nucleus to the cytoplasm, or vice versa, and some are rapidly degraded. For details of known cell cycle control components and interactions, see Kohn, Molecular Biology of the Cell (1999), 10, 2703-2734.

Accurate determination of cell cycle status is a key requirement for investigating cellular processes that affect the cell cycle or are dependent on cell cycle position. Such measurements are particularly vital in drug screening applications where:
i) substances which directly or indirectly modify cell cycle progression are desired, for example, for investigation as potential anti-cancer treatments;
ii) drug candidates are to be checked for unwanted effects on cell cycle progression; and/or
iii) it is suspected that an agent is active or inactive towards cells in a particular phase of the cell cycle.

Traditionally, cell cycle status for cell populations has been determined by flow cytometry using fluorescent dyes which stain the DNA content of cell nuclei (Barlogie, B. et al, Cancer Res., (1983), 43(9), 3982-97). Flow cytometry yields quantitative information on the DNA content of cells and hence allows determination of the relative numbers of cells in the G1, S and G2+M phases of the cell cycle. However, this analysis is a destructive non-dynamic process and requires serial sampling of a population to determine cell cycle status with time. A further disadvantage of flow cytometry techniques relates to the indirect and inferred assignment of cell cycle position of cells based on DNA content. Since the DNA content of cell nuclei varies through the cell cycle in a reasonably predictable fashion, ie. cells in G2 or M have twice the DNA content of cells in G1, and cells undergoing DNA synthesis in S phase have an intermediate amount of DNA, it is possible to monitor the relative distribution of cells between different phases of the cell cycle. However, the technique does not allow precision in determining the cell cycle position of any individual cell due to ambiguity in assigning cells to G2 or M phases and to further imprecision arising from inherent variation in DNA content from cell to cell within a population which can preclude precise discrimination between cells which are close to the boundary between adjacent phases of the cell cycle. Additionally, variations in DNA content and DNA staining between different cell types from different tissues or organisms require that the technique is optimised for each cell type, and can complicate direct comparisons of data between cell types or between experiments (Herman, Cancer (1992), 69(6), 1553-1556). Flow cytometry is therefore suitable for examining the overall cell cycle distribution of cells within a population, but cannot be used to monitor the precise cell cycle status of an individual cell over time.

EP 798386 describes a method for the analysis of the cell cycle of cell sub-populations present in heterogeneous cell samples. This method uses sequential incubation of the sample with fluorescently labelled monoclonal antibodies to identify specific cell types and a fluorochrome that specifically binds to nucleic acids. This permits determination of the cell cycle distribution of sub-populations of cells present in the sample. However, as this method utilises flow cytometry, it yields only non-dynamic data and requires serial measurements to be performed on separate samples of cells to determine variations in the cell cycle status of a cell population with time following exposure to an agent under investigation for effects on cell cycle progression.

A number of researchers have studied the cell cycle using traditional reporter enzymes that require the cells to be fixed or lysed. For example Hauser & Bauer (Plant and Soil, (2000), 226, 1-10) used β-glucuronidase (GUS) to study cell division in a plant meristem and Brandeis & Hunt (EMBO J., (1996), 15, 5280-5289) used chloramphenical acetyl transferase (CAT) fusion proteins to study variations in cyclin levels. U.S. Pat. No. 6,048,693 describes a method for screening for compounds affecting cell cycle regulatory proteins, wherein expression of a reporter gene is linked to control elements which are acted on by cyclins or other cell cycle control proteins. In this method, temporal expression of a reporter gene product is driven in a cell cycle specific fashion and compounds acting on one or more cell cycle control components may increase or decrease expression levels.

U.S. Pat. No. 6,159,691 describes nuclear localisation signals (NLS) derived from the cell cycle phase-specific transcription factors DP-3 and E2F-1 and claims a method for assaying for putative regulators of cell cycle progression. In this method, nuclear localisation signals (NLS) derived from the cell cycle phase specific transcription factors DP-3 and E2F-1 may be used to assay the activity of compounds which act to increase or decrease nuclear localisation of specific NLS sequences from DP-3 and E2F-1 fused to a detectable marker.

Jones et al (Nat Biotech., (2004), 23, 306-312) describe a fluorescent biosensor of mitosis based on a plasma membrane targeting signal and an SV40 large T antigen NLS fused to EYFP. Throughout the cell cycle the reporter resides in the nucleus but translocates to the plasma membrane during mitosis, between nuclear envelope breakdown and re-formation.

WO 03/031612 describes DNA reporter constructs and methods for determining the cell cycle position of living mammalian cells by means of cell cycle phase-specific expression control elements and destruction control elements.

Gu et al. (Mol Biol Cell., 2004,15, 3320-3332) have recently investigated the function of human DNA helicase B (HDHB) and shown that it is primarily nuclear in G1 and cytoplasmic in S and G2 phases, that it resides in nuclear foci induced by DNA damage, that the focal pattern requires HDHB activity, and that HDHB localization is regulated by CDK phosphorylation.

None of the preceding methods specifically describe sensors which can be stably integrated into the genome and used to indicate G1, S and G2 phases of the cell cycle. Consequently, methods are required that enable these phases of the cell cycle to be determined non-destructively in a single living mammalian cell, allowing the same cell to be repeatedly interrogated over time, and which enable the study of the effects of agents having potentially desired or undesired effects on the cell cycle. Methods are also required that permit the parallel assessment of these effects for a plurality of agents.

SUMMARY OF THE INVENTION

The present invention describes a method which utilises key components of the cell cycle regulatory machinery in defined combinations to provide novel means of determining cell cycle status for individual living cells in a non-destructive process providing dynamic read out.

The present invention further provides proteins, DNA constructs, vectors, and stable cell lines expressing such proteins, that exhibit translocation of a detectable reporter molecule in a cell cycle phase specific manner, by direct linkage of the reporter signal to a G1/S cell cycle phase dependent location control sequence. This greatly improves the precision of determination of cell cycle phase status and allows continuous monitoring of cell cycle progression in individual cells. Furthermore, it has been found that key control elements can be isolated and abstracted from functional elements of the cell cycle control mechanism to permit design of cell cycle phase reporters which are dynamically regulated and operate in concert with, but independently of, endogenous cell cycle control components, and hence provide means for monitoring cell cycle position without influencing or interfering with the natural progression of the cell cycle.

According to a first aspect of the present invention, there is provided a polypeptide construct comprising a detectable live-cell reporter molecule linked via a group having a molecular mass of less than 112,000 Daltons to at least one cell cycle phase-dependent location control element, the location of which said element changes during G1 and S phase, wherein the translocation of said construct within a mammalian cell is indicative of the cell cycle position.

It will be understood that translocation is defined as the detectable movement of the reporter from one sub-cellular location to another, typically from the nucleus to the cytoplasm or vice versa. It will be further understood that the term 'live cell', as it relates to a reporter molecule, defines a reporter molecule which produces a detectable signal in living cells, or a reporter, such as an antigenic tag, that is expressed in living cells and can be detected after fixation through immunological methods, and is thus suitable for use in imaging systems, such as the IN Cell Analyzer (GE Healthcare).

Suitably, said group has a molecular mass of less than 100,000 Daltons.

Suitably, the group has a molecular mass of less than 50,000 Daltons.

Suitably, the group has a molecular mass of less than 25,000 Daltons.

Suitably, the group has a molecular mass of less than 10,000 Daltons.

Suitably, the group has a molecular mass of less than 1,000 Daltons.

Suitably, the group has a molecular mass of less than 700 Daltons.

Suitably, the group has a molecular mass of less than 500 Daltons.

Preferably, the group is a polypeptide. The polypeptide group should be relatively small and comprise amino acids that allow flexibility and/or rotation of the reporter molecule relative to the cell cycle phase-dependent location control element. More preferably, the polypeptide group is a heptapeptide. Most preferably, said heptapeptide group is Gycine-Asparagine-Glycine-Glycine-Asparagine-Alanine-Serine (GNGGNAS; SEQ ID NO: 18). As stated above, any amino acids which allow flexibility and/or rotation of the reporter molecule relative to the location control element may be used in the polypeptide. Suitably, the cell cycle phase-specific dependent location control element is selected from the group of peptides consisting of Rag2, Chaf1B, Fen1, PPP1 R2, helicase B, sgk, CDC6 or motifs therein such as the phosphorylation-dependent subcellular localization domain of the C-terminal special control region of helicase B (PSLD). Helicase B is known to cause uncontrolled DNA licensing and may be detrimental to cell survival when over-expressed. Therefore, preferably, the cell cycle phase-dependent location control element is the phosphorylation-dependent subcellular localization domain of the C-terminal spacial control region of helicase B (PSLD).

A human helicase B homolog has been reported and characterised ((Taneja et al J. Biol. Chem., (2002), 277, 40853-40861); the nucleic acid sequence (NM 033647) and the corresponding protein sequence are given in SEQ ID No. 1 and SEQ ID No. 2, respectively. The report demonstrates that helicase activity is needed during G1 to promote the G1/S transition. Gu et al (Mol. Biol. Cell., (2004), 15, 3320-3332) have shown that a small C-terminal region of the helicase B gene termed the phosphorylation-dependent subcellular localization domain (PSLD) is phosphorylated by Cdk2/cyclin E and contains NLS and NES sequences. Gu et al (Mol. Biol. Cell., (2004), 15, 3320-3332) carried out studies on cells that had been transiently transfected with plasmid encoding an EGFP-βGal-PSLD fusion (beta-galactosidase (βGal) was included in the construct as an inert group to make the whole fusion protein similar in size to the complete helicase B) expressed from a CMV promoter. Cells in G1 exhibited EGFP signal predominantly in the nucleus, whilst cells in other phases of the cell cycle exhibited predominantly cytoplasmic EGFP signal. These researchers concluded that the PSLD was directing translocation of the reporter from the nucleus to the cytoplasm around the G1/S phase transition of the cell cycle.

Suitably, the live-cell reporter molecule is selected from the group consisting of fluorescent protein, enzyme and antigenic tag. Preferably, the fluorescent protein is derived from *Aequoria Victoria, Renilla reniformis* or other members of the classes Hydrozoa and Anthozoa (Labas et al., Proc. Natl. Acad. Sci, (2002), 99, 4256-4261). More preferably, the fluorescent protein is EGFP (BD Clontech), Emerald (Tsien, Annu. Revs. Biochem., (1998), 67, 509-544) or J-Red (Evrogen). Most preferably, the fluorescent protein is selected from the group consisting of Green Fluorescent Protein (GFP), Enhanced Green Fluorescent Protein (EGFP), Emerald and J-Red.

Suitably, the reporter is an enzyme reporter such as halotag (Promega).

Suitably, the reporter molecule is EGFP or J-Red and the cell cycle phase-dependent location control element is PSLD.

Suitably, the reporter molecule is tandemized (i.e. present as a tandem repeat).

A polypeptide construct comprising the amino acid sequence of SEQ ID No. 5.

According to a second aspect of the present invention, there is provided a nucleic acid construct encoding any of the polypeptide constructs as hereinbefore described.

Suitably, said nucleic acid construct additionally comprises and is operably linked to and under the control of at least one cell cycle independent expression control element.

The term, 'operably linked' indicates that the elements are arranged so that they function in concert for their intended purposes, e.g. transcription initiates in a promoter and proceeds through the DNA sequence coding for the reporter molecule of the invention.

Suitably, the expression control element controls transcription over an extended time period with limited variability in levels of transcription throughout the cell cycle. Preferably, the expression control element is the ubiquitin C or CMV I/E promoter which provide transcription over an extended period which is required for the production of stable cell lines.

Preferably, the nucleic acid construct comprises a Ubiquitin C promoter, and sequences encoding PSLD and EGFP or J-Red.

Optionally, the nucleic acid construct comprises a CMV promoter, and sequences encoding PSLD and EGFP or J-Red.

In a third aspect of the present invention, there is provided a vector comprising any of the nucleic acid constructs as hereinbefore described. Suitably, said vector is either a viral vector or a plasmid. Suitably, said viral vector is an adenoviral vector or a lentiviral vector.

Optionally, the vector additionally contains a drug resistance gene that is functional in eukaryotic cells, preferably a drug resistance gene that is functional in mammalian cells.

Expression vectors may also contain other nucleic acid sequences, such as polyadenylation signals, splice donor/splice acceptor signals, intervening sequences, transcriptional enhancer sequences, translational enhancer sequences and the like. Optionally, the drug resistance gene and reporter gene may be operably linked by an internal ribosome entry site (IRES), (Jang et al., J. Virology, (1988), 62, 2636-2643) rather than the two genes being driven by separate promoters. The pIRES-neo and pIRES vectors commercially available from Clontech may be used.

In a fourth aspect of the present invention, there is provided a host cell transfected with a nucleic acid construct as hereinbefore described. The host cell into which the construct or the expression vector containing such a construct is introduced may be any mammalian cell which is capable of expressing the construct.

The prepared DNA reporter construct may be transfected into a host cell using techniques well known to the skilled person. These techniques may include: electroporation (Tur-Kaspa et al, Mol. Cell Biol. (1986), 6, 716-718), calcium phosphate based methods (eg. Graham and Van der Eb, Virology, (1973), 52, 456-467), direct microinjection, cationic lipid based methods (eg. the use of Superfect (Qiagen) or Fugene6 (Roche) and the use of bombardment mediated gene transfer (Jiao et al, Biotechnology, (1993), 11, 497-502). A further alternative method for transfecting the DNA construct into cells, utilises the natural ability of viruses to enter cells. Such methods include vectors and transfection protocols based on, for example, Herpes simplex virus (U.S. Pat. No. 5,288,641), cytomegalovirus (Miller, Curr. Top. Microbiol. Immunol., (1992), 158, 1), vaccinia virus (Baichwal and Sugden, 1986, in Gene Transfer, ed. R. Kucherlapati, New York, Plenum Press, p117-148), and adenovirus and adeno-associated virus (Muzyczka, Curr. Top. Microbiol. Immunol., (1992), 158, 97-129).

Examples of suitable recombinant host cells include HeLa cells, Vero cells, Chinese Hamster ovary (CHO), U20S, COS, BHK, HepG2, NIH 3T3 MDCK, RIN, HEK293 and other mammalian cell lines that are grown in vitro. Preferably the host cell is a human cell. Such cell lines are available from the American Tissue Culture Collection (ATCC), Bethesda, Md., U.S.A. Cells from primary cell lines that have been established after removing cells from a mammal followed by culturing the cells for a limited period of time are also intended to be included in the present invention.

In a preferred embodiment, the cell line is a stable cell line comprising a plurality of host cells according to the fourth aspect.

Cell lines which exhibit stable expression of a cell cycle position reporter may also be used in establishing xenografts of engineered cells in host animals using standard methods. (Krasagakis, K. J et al, Cell Physiol., (2001), 187(3), 386-91; Paris, S. et al, Clin. Exp. Metastasis, (1999), 17(10), 817-22). Xenografts of tumour cell lines engineered to express cell cycle position reporters will enable establishment of model systems to study tumour cell division, stasis and metastasis and to screen new anticancer drugs.

In a fifth aspect of the present invention, there is provided the use of a polypeptide as hereinbefore described for determining the cell cycle position of a mammalian cell.

Use of engineered cell lines or transgenic tissues expressing a cell cycle position reporter as allografts in a host animal will permit study of mechanisms affecting tolerance or rejection of tissue transplants (Pye & Watt, J. Anat., (2001), 198 (Pt 2), 163-73; Brod, S. A. et al, Transplantation (2000), 69(10), 2162-6).

According to a sixth aspect of the present invention, there is provided a method for determining the cell cycle position of a mammalian cell, said method comprising:

a) expressing in a cell a nucleic acid construct as hereinbefore described; and b) determining the cell cycle position by monitoring signals emitted by the reporter molecule.

To perform the method for determining the cell cycle position of a cell according to the sixth aspect, cells transfected with the DNA reporter construct may be cultured under conditions and for a period of time sufficient to allow expression of the reporter molecule at a specific stage of the cell cycle.

Typically, expression of the reporter molecule will occur between 16 and 72 hours post transfection, but may vary depending on the culture conditions. If the reporter molecule is based on a green fluorescent protein sequence the reporter may take a defined time to fold into a conformation that is fluorescent. This time is dependent upon the primary sequence of the green fluorescent protein derivative being used. The fluorescent reporter protein may also change colour with time (see for example, Terskikh, Science, (2000), 290, 1585-8) in which case imaging is required at specified time intervals following transfection.

If the reporter molecule produces a fluorescent signal in the method of the sixth aspect, either a conventional fluorescence microscope, or a confocal based fluorescence microscope may be used to monitor the emitted signal. Using these techniques, the proportion of cells expressing the reporter molecule, and the location of the reporter can be determined. In the method according to the present invention, the fluorescence of cells transformed or transfected with the DNA construct may suitably be measured by optical means in for example; a spectrophotometer, a fluorimeter, a fluorescence microscope, a cooled charge-coupled device (CCD) imager (such as a scanning imager or an area imager), a fluorescence activated cell sorter, a confocal microscope or a scanning confocal device, where the spectral properties of the cells in culture may be determined as scans of light excitation and emission.

In the embodiment of the invention wherein the nucleic acid reporter construct comprises a drug resistance gene, following transfection and expression of the drug resistance gene (usually 1-2 days), cells expressing the modified reporter gene may be selected by growing the cells in the presence of an antibiotic for which transfected cells are resistant due to the presence of a selectable marker gene. The purpose of adding the antibiotic is to select for cells that express the reporter gene and that have, in some cases, integrated the reporter gene, with its associated promoter, into the genome of the cell line. Following selection, a clonal cell line expressing the construct can be isolated using standard techniques. The clonal cell line may then be grown under standard conditions and will express reporter molecule and produce a detectable signal at a specific point in the cell cycle.

Cells transfected with the nucleic acid reporter construct according to the present invention may be grown in the absence and/or the presence of a test agent to be studied and whose effect on the cell cycle of a cell is to be determined. By determining the proportion of cells expressing the reporter molecule and the localisation of the signal within the cell, it is possible to determine the effect of a test agent on the cell cycle of the cells, for example, whether the test system arrests the cells in a particular stage of the cell cycle, or whether the effect is to speed up or slow down cell division.

Thus, according to a seventh aspect of the present invention, there is provided a method of determining the effect of a test agent on the cell cycle position of a mammalian cell, the method comprising:
a) expressing in the cell in the absence and in the presence of the test agent a nucleic acid reporter construct as hereinbefore described; and
b) determining the cell cycle position by monitoring signals emitted by the reporter molecule wherein a difference between the emitted signals measured in the absence and in the presence of the test agent is indicative of the effect of the test agent on the cell cycle position of the cell.

The term 'test agent' should be construed as a form of electromagnetic radiation or as a chemical entity. Preferably, the test agent is a chemical entity selected from the group consisting of drug, nucleic acid, hormone, protein and peptide. The test agent may be applied exogenously to the cell or may be a peptide or protein that is expressed in the cell under study.

In an eighth aspect of the present invention, there is provided a method of determining the effect of a test agent on the cell cycle position of a mammalian cell, the method comprising:
a) expressing in said cell in the presence of said test agent a nucleic acid reporter construct as hereinbefore described;
b) determining the cell cycle position by monitoring signals emitted by the reporter molecule, and
c) comparing the emitted signal in the presence of the test agent with a known value for the emitted signal in the absence of the test agent;

wherein a difference between the emitted signal measured in the presence of the test agent and the known value in the absence of the test agent is indicative of the effect of the test agent on the cell cycle position of the cell.

In a ninth aspect of the present invention, there is provided a method of determining the effect of a test agent on the cell cycle position of a mammalian cell, the method comprising:
a) providing cells containing a nucleic acid reporter construct as hereinbefore described;
b) culturing first and second populations of the cells respectively in the presence and absence of a test agent and under conditions permitting expression of the nucleic acid reporter construct; and
c) measuring the signals emitted by the reporter molecule in the first and second cell populations;

wherein a difference between the emitted signals measured in the first and second cell populations is indicative of the effect of the test agent on the cell cycle position of the cell.

According to a tenth aspect of the present invention, there is provided a method of determining the effect of the mammalian cell cycle on a cellular process measurable by a first detectable reporter which is known to vary in response to a test agent, the method comprising:
a) expressing in the cell in the presence of the test agent a second nucleic acid reporter construct as hereinbefore described;
b) determining the cell cycle position by monitoring signals emitted by the second reporter molecule; and
c) monitoring the signals emitted by the first detectable reporter, wherein the relationship between cell cycle position determined by step b) and the signal emitted by the first detectable reporter is indicative of whether or not said cellular process is cell cycle dependent.

In an eleventh aspect of the present invention, there is provided the use of a polypeptide as hereinbefore described for measuring CDK2 activity in a cell.

According to a twelfth aspect of the present invention, there is provided a method for measuring CDK2 activity in a cell, said method comprising the steps of
a) expressing a nucleic acid construct in a cell as hereinbefore described' and
b) determining CDK2 activity by monitoring signals emitted by the reporter molecule.

According to a thirteenth aspect of the present invention, there is provided a method for determining the effect of a test agent on CDK2 activity of a mammalian cell, said method comprising:

a) expressing in said cell in the absence and in the presence of said test agent a nucleic acid construct as hereinbefore described; and b) determining CDK2 activity by monitoring signals emitted by the reporter molecule wherein a difference between the emitted signals measured in the absence and in the presence of said test agent is indicative of the effect of the test agent on the activity of CDK2.

In a fourteenth aspect of the present invention, there is provided a method of determining the effect of a test agent on CDK2 activity of a mammalian cell, said method comprising:

a) expressing in said cell in the presence of said test agent a nucleic acid construct as hereinbefore described; and b) determining the cell cycle position by monitoring signals emitted by the reporter molecule, c) comparing the emitted signal in the presence of the test agent with a known value for the emitted signal in the absence of the test agent;

wherein a difference between the emitted signal measured in the presence of the test agent and said known value in the absence of the test agent is indicative of the effect of the test agent on the CDK2 activity of the cell.

BRIEF DESCRIPTION OF THE DRAWINGS

The invention is further illustrated by reference to the following examples and figures in which.

(A) Cytoplasmic and nuclear extracts of U2OS cells were analyzed by denaturing gel electrophoresis and western blotting with antibody against recombinant HDHB, α-tubulin, and PCNA. Immunoreactive proteins were detected by chemiluminescence.

(B) GFP-tagged HDHB microinjected and transiently expressed in U2OS cells were visualized by fluorescence microscopy. Nuclei were stained with Hoechst dye. Bar, 10 μm.

(C) FLAG-tagged HDHB microinjected and transiently expressed in U2OS cells were visualized by fluorescence microscopy.

Figure 2:
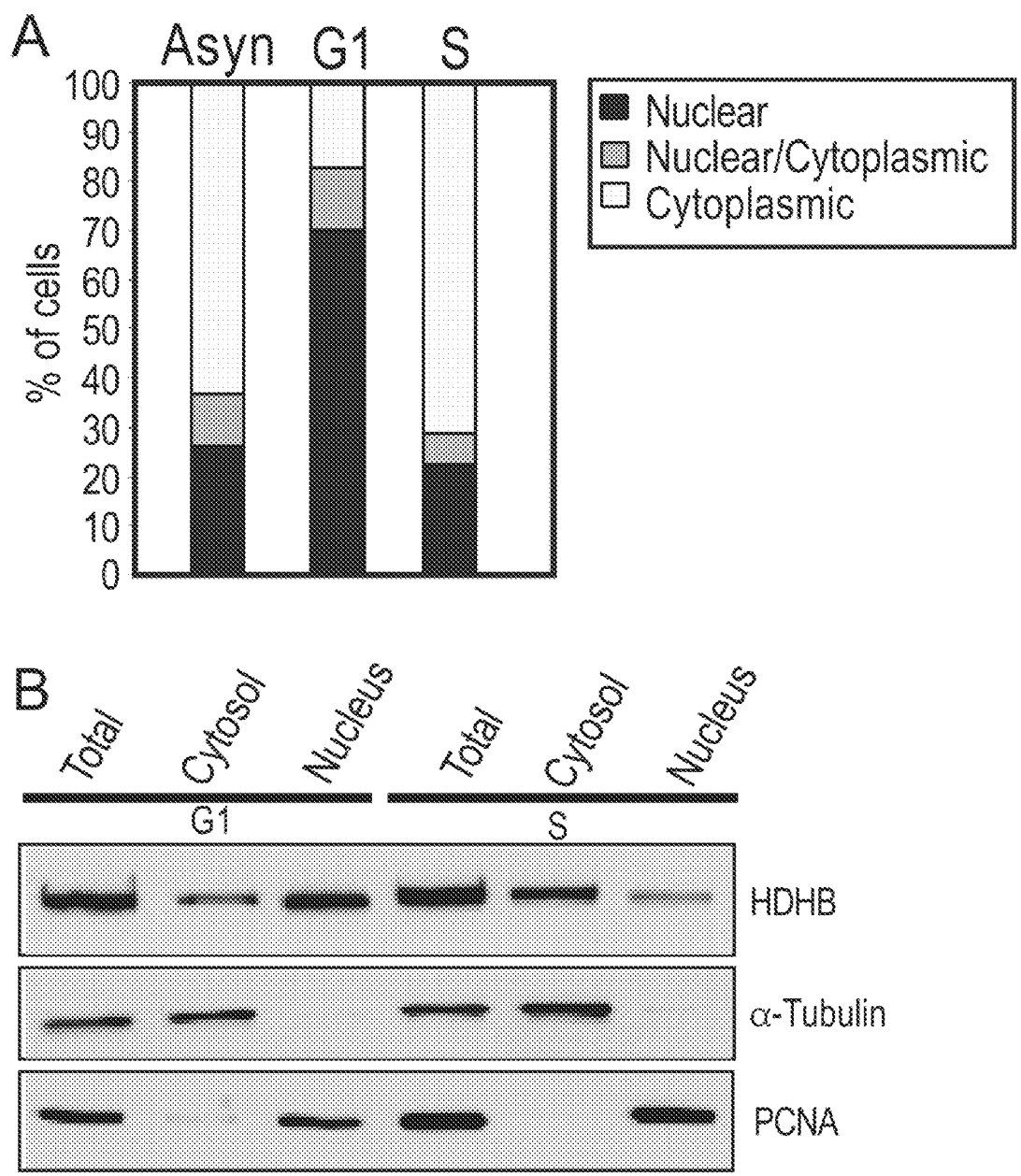

FIG. 2—The subcellular localization of GFP-HDHB is cell cycle-dependent.

(A) Subcellular localization of transiently expressed GFP-tagged HDHB in asynchronous, G1, and S phase U2OS cells was quantified. The number of GFP-positive cells with a given distribution pattern was expressed as a percentage of the total number of GFP-positive cells (>100 cells).

(B) Cytoplasmic and nuclear extracts of synchronized U2OS cells (G1 and S phase) were analyzed by denaturing gel electrophoresis and western blotting with antibody against recombinant HDHB, α-tubulin, and PCNA. Immunoreactive proteins were detected by chemiluminescence.

Figure 3:
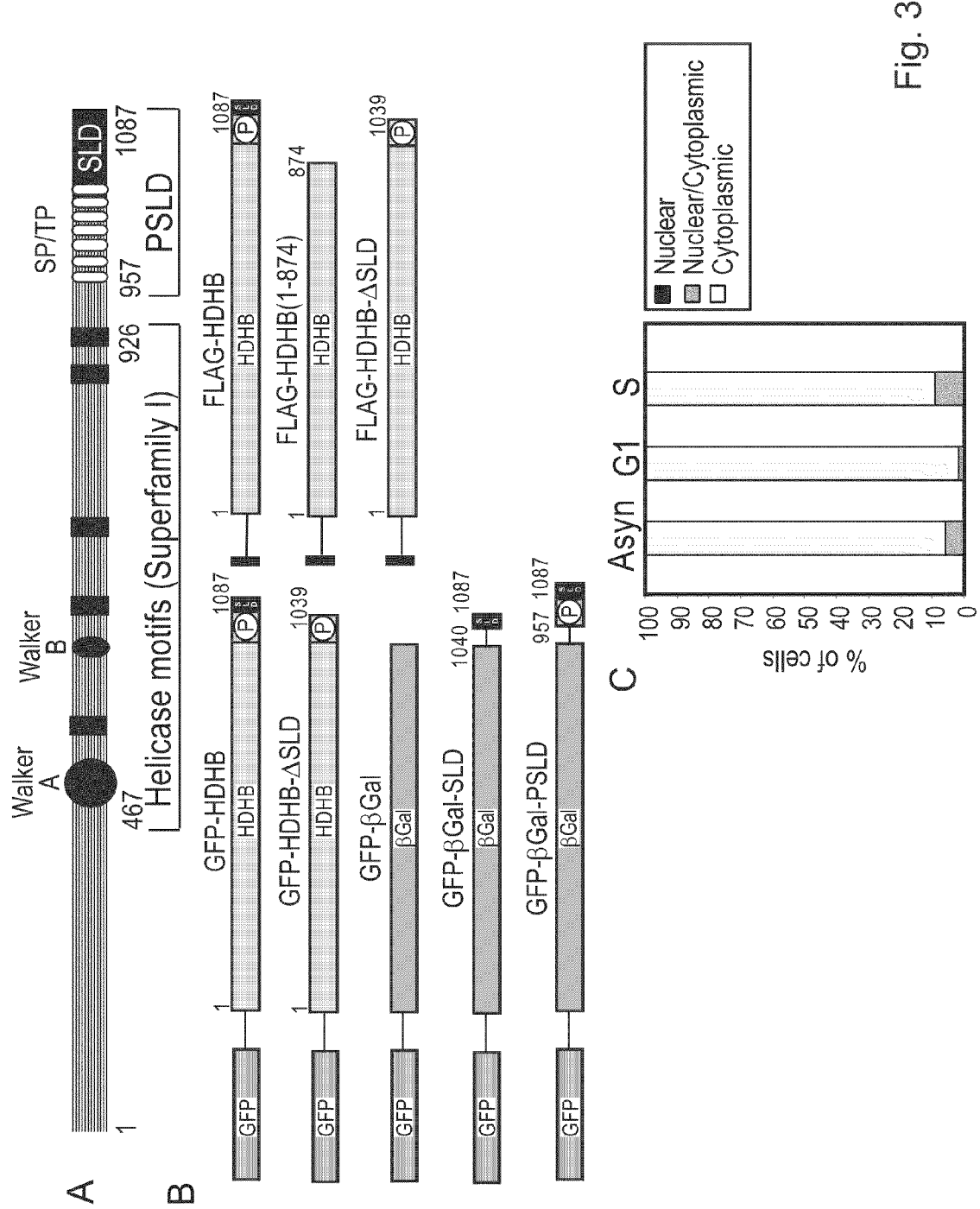

FIG. 3—Identification of a domain required for nuclear localization of HDHB.

(A) Schematic representation of the HDHB protein showing seven potential phosphorylation sites for CDK (SP or TP), the putative subcellular localization domain (SLD) and phosphorylated SLD (PSLD), the Walker A and Walker B helicase motifs. Amino acid residue numbers are indicated below protein.

(B) GFP- and FLAG-tagged HDHB and C-terminal truncation mutants generated in study. The C terminus of HDHB SLD (residues 1040-1087) and PSLD (residues 957-1087) was fused to a GFP-βGal reporter to create GFP-βGal-SLD and GFP-βGal-PSLD respectively.

(C) The subcellular localization of transiently expressed GFP-HDHB-ASLD in asynchronous, G1, and S phase U2OS cells was quantified and expressed as a percentage of the total number of GFP-positive cells.

Figure 4:
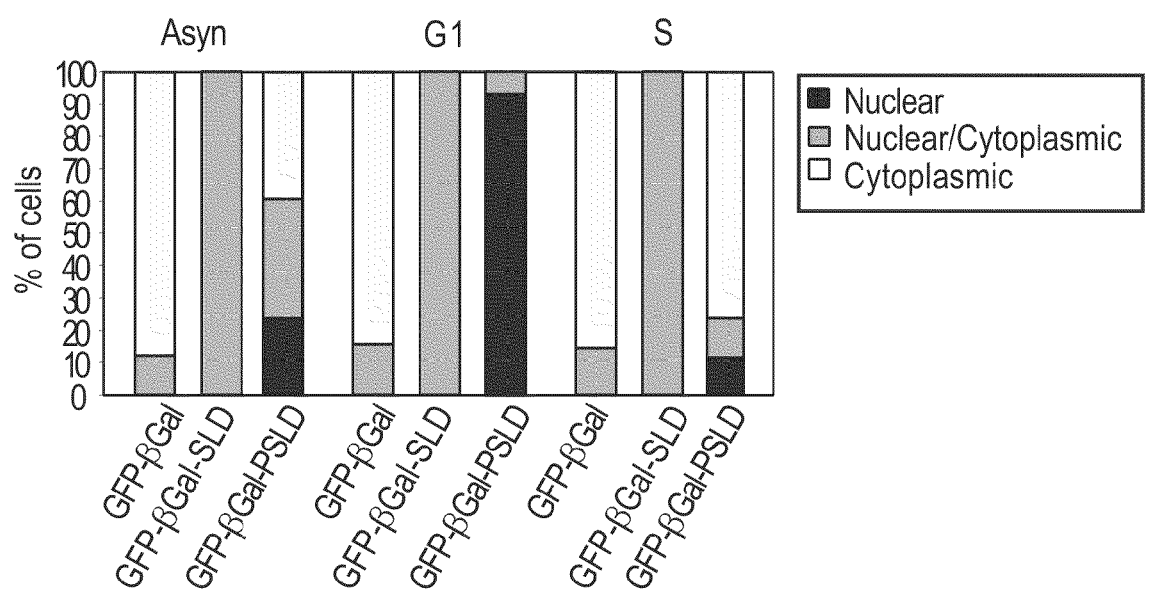

FIG. 4—GFP-βGal-PSLD subcellular localization pattern varies with the cell cycle.

(A) The subcellular localization of transiently expressed GFP-βGal, GFP-βGal-SLD, and GFP-βGal-PSLD in asynchronous, G1, and S phase U2OS cells was quantified and expressed as a percentage of the total number of GFP-positive cells.

Figure 5:
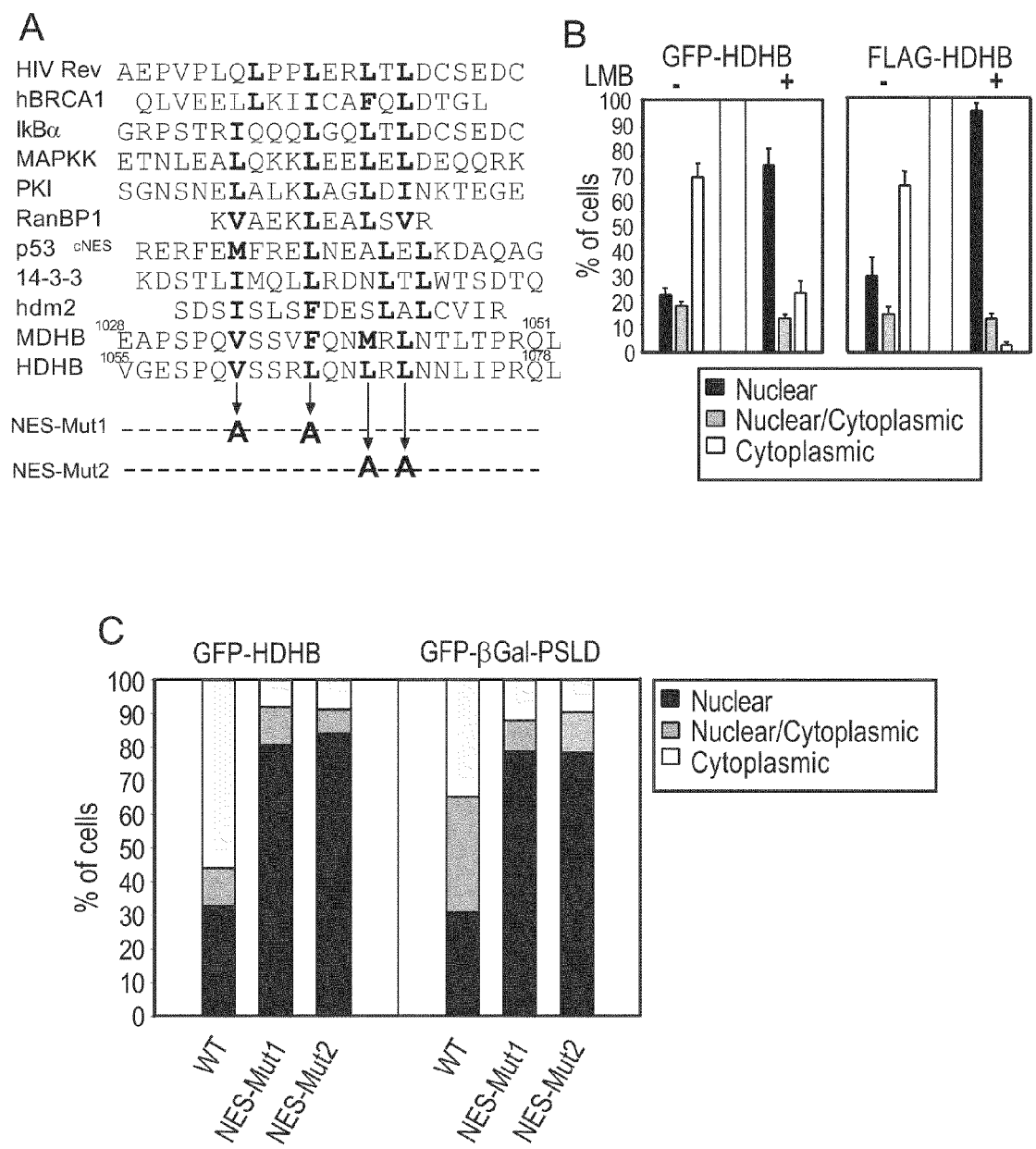

FIG. 5—Identification of a functional rev-type nuclear export signal (NES) in SLD of HDHB.

(A) Alignment of the putative NES in HDHB with those identified in other cell cycle-related proteins (Henderson and Eleftheriou, 2000; Fabbro and Henderson, 2003). Superscripts above the amino acid sequence indicate residue numbers. Thick arrows point to the conserved aliphatic residues in the NES. Two pairs of residues in the putative NES in HDHB were mutated to alanine as indicated by the thin arrows to create Mut1 and Mut2. HIV Rev: SEQ ID NO: 7; hBRCA1: SEQ ID NO: 8; IkBα: SEQ ID NO: 9; MAPKK: SEQ ID NO: 10; PKI: SEQ ID NO: 11; RanBP1: SEQ ID NO: 12; p53 cNES: SEQ ID NO: 13; 14-3-3: SEQ ID NO: 14; hdm2: SEQ ID NO: 15; MDHB: SEQ ID NO: 16; HDHB: SEQ ID NO: 17.

(B) GFP- and FLAG-tagged HDHB were transiently expressed in asynchronously growing U2OS cells with (+) or without (−) LMB to inhibit CRM1-mediated nuclear export. The subcellular localization of GFP-HDHB and FLAG-HDHB in asynchronous, G1, and S phase cells was quantified and expressed as a percentage of the total number of GFP-positive cells in that sample.

(C) The subcellular localization of wild type and mutant GFP-HDHB and GFP-βGal-PSLD in asynchronous U2OS cells was quantified and expressed as a percentage of the total number of GFP-positive cells in that sample.

Figure 6:
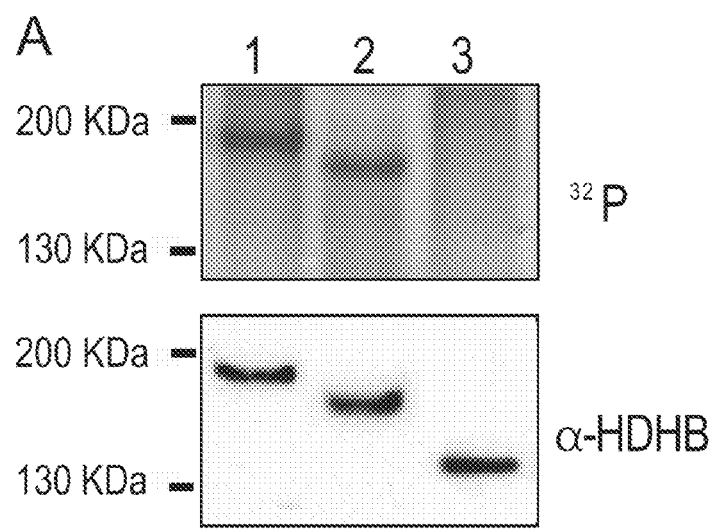
Figure 6:
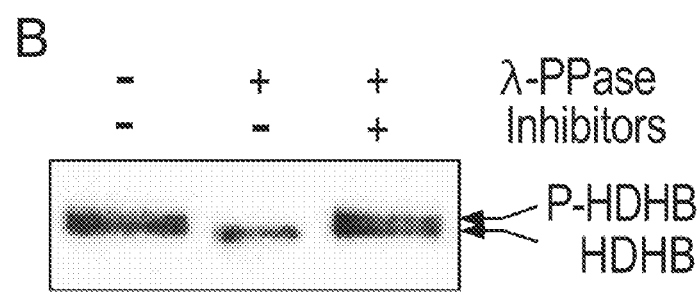
Figure 6:
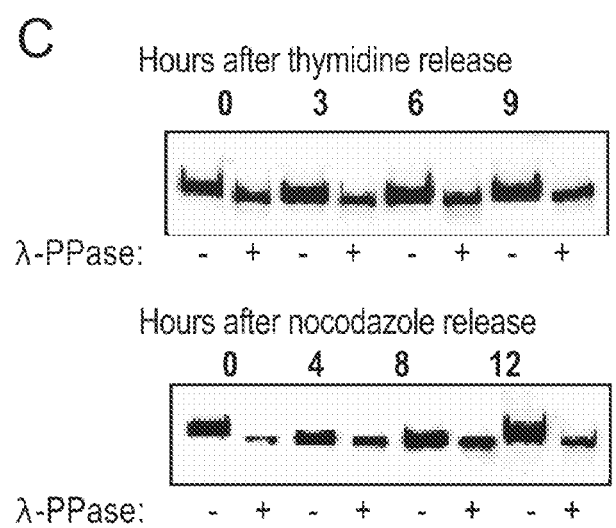

FIG. 6—Cell cycle-dependent phosphorylation of FLAG-HDHB in vivo.

(A) U2OS cells transiently expressing FLAG-HDHB (lane 1) and its truncation mutants 1-1039 (lane 2) and 1-874 (lane 3) were labeled with [$^{32}$P] orthophosphate. Cell extracts were immunoprecipitated with anti-FLAG resin. The precipitated proteins were separated by 7.5% SDS-PAGE, transferred to a PVDF membrane, and detected by autoradiography (top) or western blotting (bottom). The positions of marker proteins of known molecular mass are indicated at the left.

(B) FLAG-HDHB expressed in U2OS cells was immunoprecipitated with anti-FLAG resin, incubated with (+) or without (−) A-phosphatase (A-PPase) in the presence (+) or absence (−) of phosphatase inhibitors, as indicated, and analyzed by SDS-PAGE and immunoblotting with anti-HDHB antibody.

(C) U2OS cells expressing FLAG-HDHB were arrested at G1/S (top) or at G2/M(bottom), and then released from the block. FLAG-HDHB was harvested at the indicated time points, immunoprecipitated with anti-FLAG resin, treated with (+) or without (−) A-PPase, and analyzed as in (B).

Figure 7:
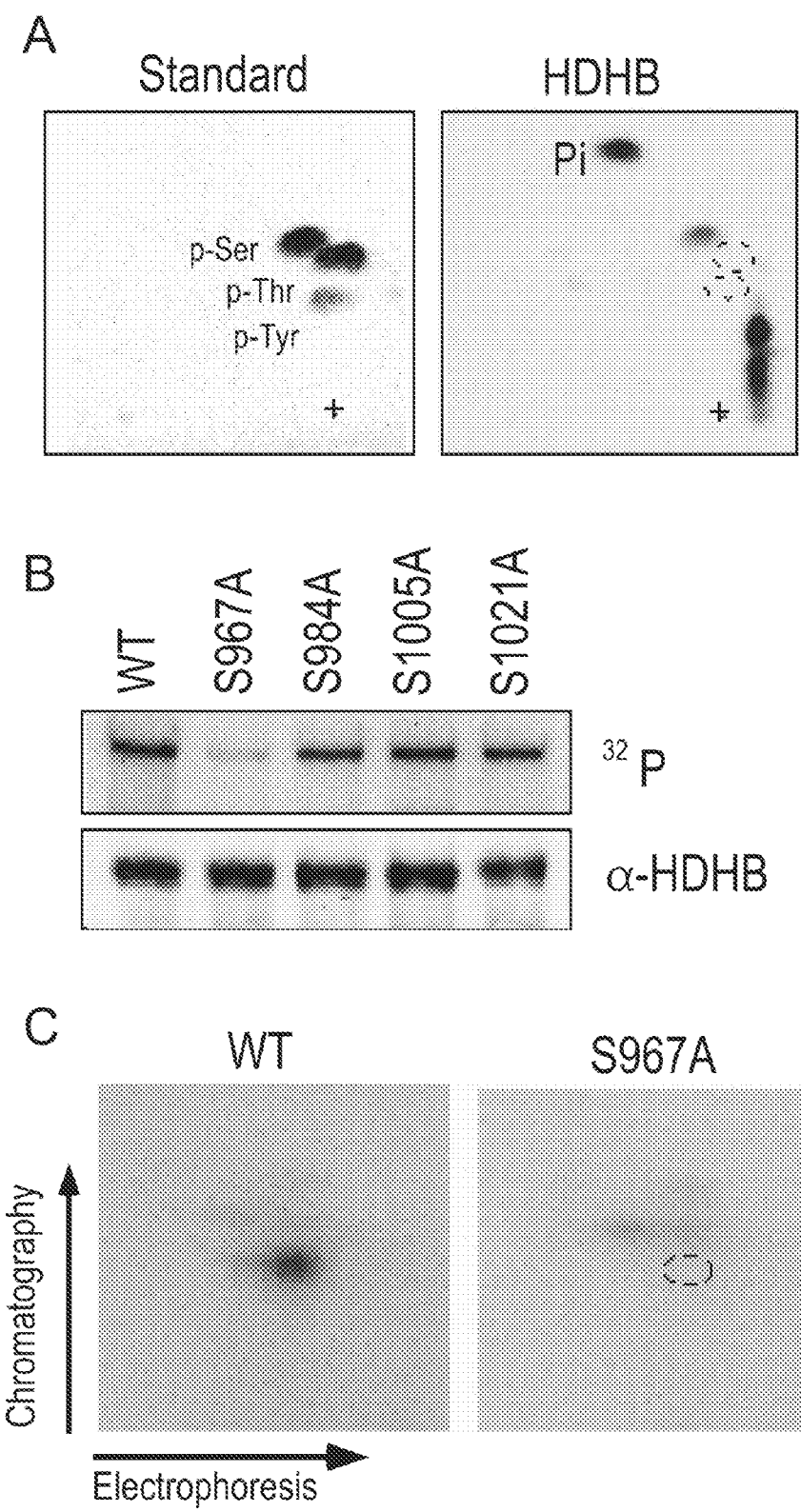

FIG. 7—Identification of S967 as a major in vivo phosphorylation site in HDHB.

(A) Phosphoamino acid markers (left) and phosphoamino acids from in vivo 32P-labeled FLAG-HDHB (right) were separated in two dimensions and visualized by autoradiography. Some incompletely hydrolyzed phosphopeptides remained near the origin (+).

(B) Wild type and mutant FLAG-HDHB proteins were radiolabeled with orthophosphate in vivo, immunoprecipitated, separated by SDS-PAGE, and analyzed by autoradiography (top) and immunoblotting with anti-HDHB (bottom).

(C) Tryptic phosphopeptides of 32P-labeled wild type and S967A mutant FLAG-HDHB were separated in two dimensions and visualized by autoradiography.

Figure 8:
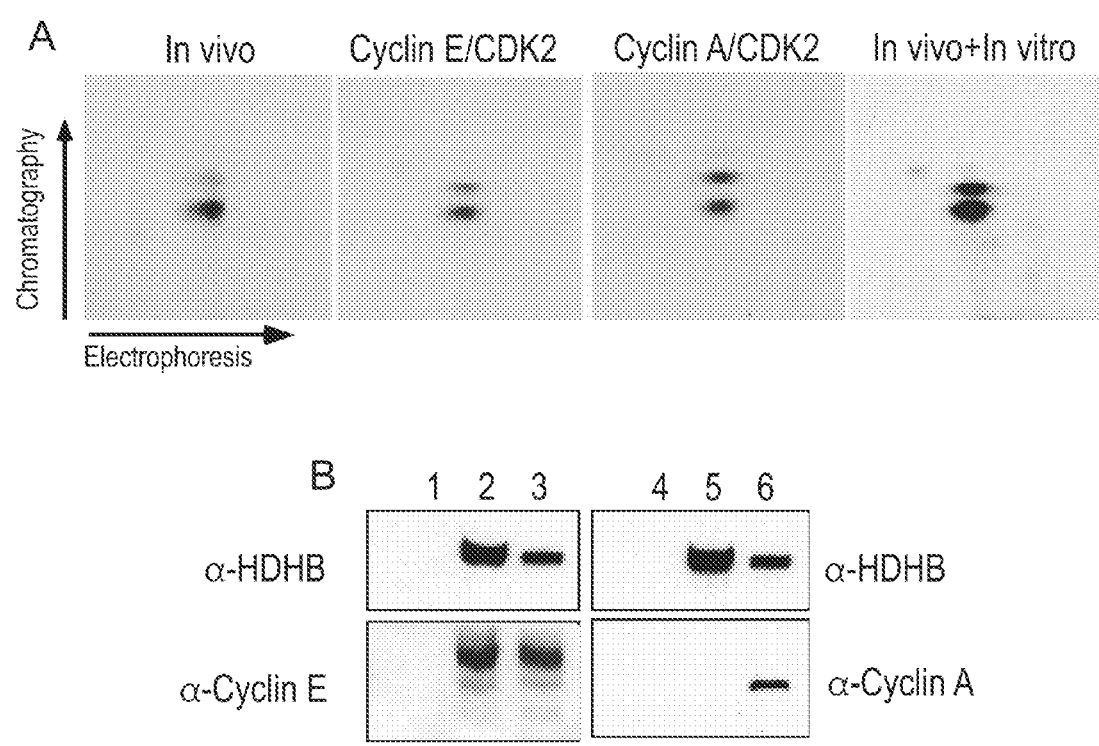

FIG. 8—Identification of cyclin E/CDK2 as the potential G1/S kinase of HDHB S967.

(A) Tryptic phosphopeptides from FLAG-HDHB phosphorylated in vivo as in FIG. 7C, or recombinant HDHB phosphorylated in vitro by purified cyclin E/CDK2 or cyclin A/CDK2, were separated in two dimensions, either individually or as a mixture, and visualized by autoradiography.

(B) Proteins that co-immunoprecipitated with FLAG vector (lanes 1, 4) or FLAG-HDHB (lanes 2, 5) expressed in U2OS cells were analyzed by immunoblotting with antibodies against HDHB (lanes 1-6), cyclin E (lanes 1-3), or cyclin A (lanes 4-6). One tenth of the cell lysate used for immunoprecipitation was analyzed in parallel as a positive control (lanes 3, 6).

Figure 9:
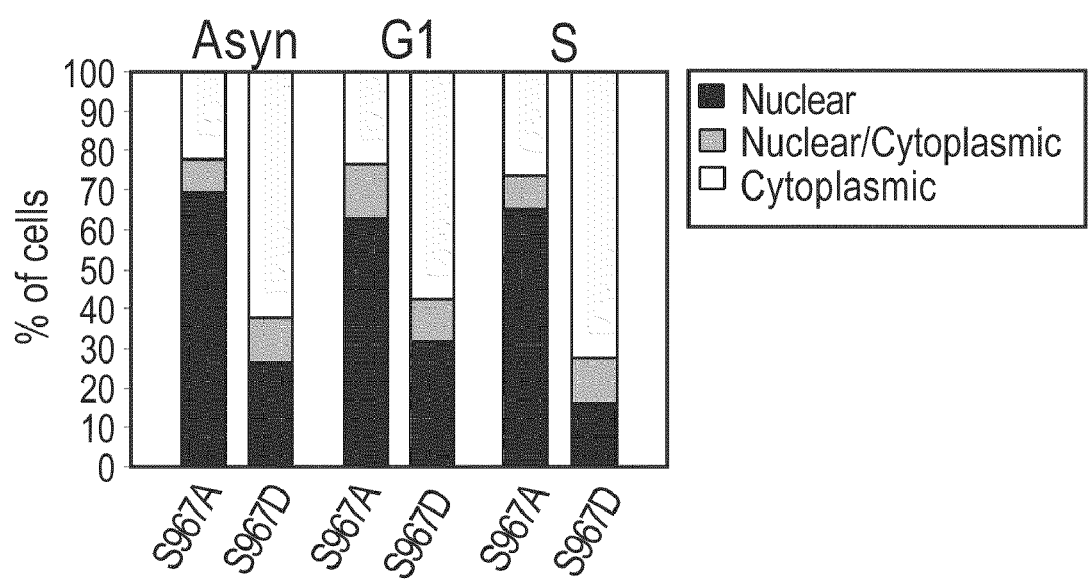

FIG. 9—The subcellular localization of HDHB is regulated by phosphorylation of S967.

(A) Subcellular localization of GFP-HDHB S967A and S967D expressed in asynchronous, G1, and S phase U2OS cells was quantified.

Figure 10:
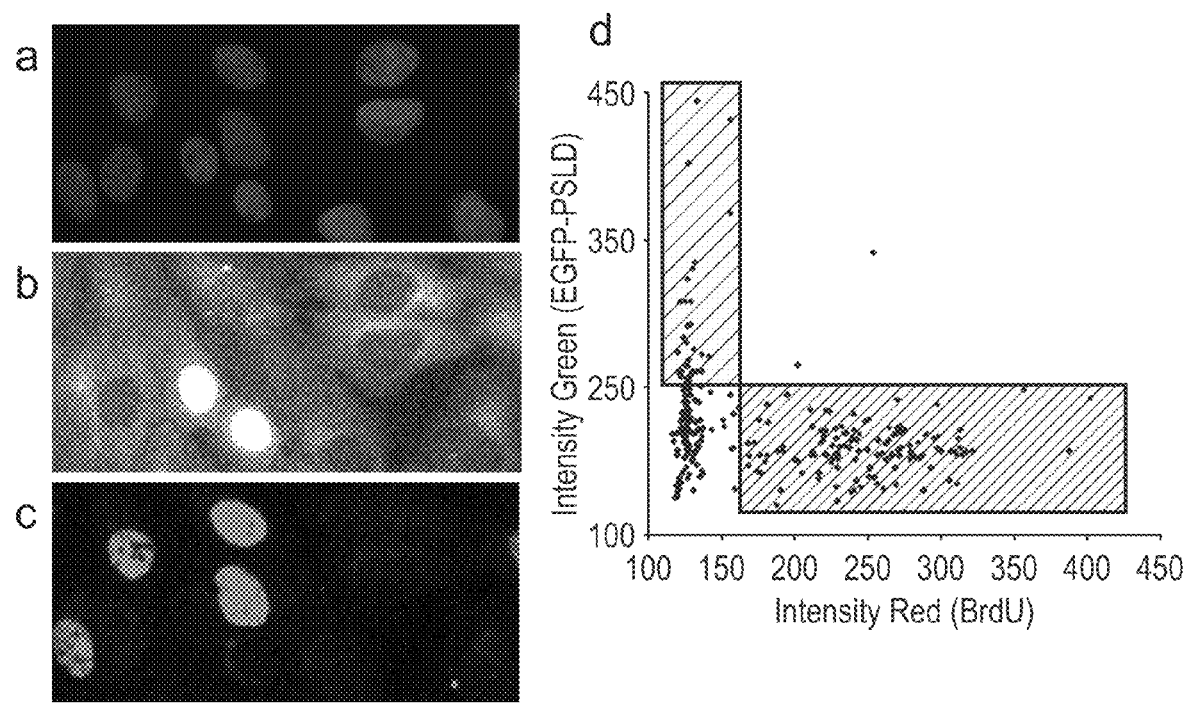

FIG. 10—Localisation of EGFP-PSLD in asynchronous U2OS cells exhibiting stable expression of the pCORON1002-EGFP-C1-PSLD vector is cell cycle dependent. Fluorescence microscopy of the same partial field of cells in which (A) nuclei were stained with Hoechst dye, (B) EGFP-PSLD was visualised, (C) nuclei were exposed to BrdU for 1 hour exposure prior to fixation and detection with Cy-5 labelled antibody to indicate cells in S-phase. (D) A graph of nuclear fluorescent intensity in both the red (Cy-5 immunofluorescent detection of BrdU) and green (EGFP-PSLD) for individual cells present in a full field of view.

Figure 11:
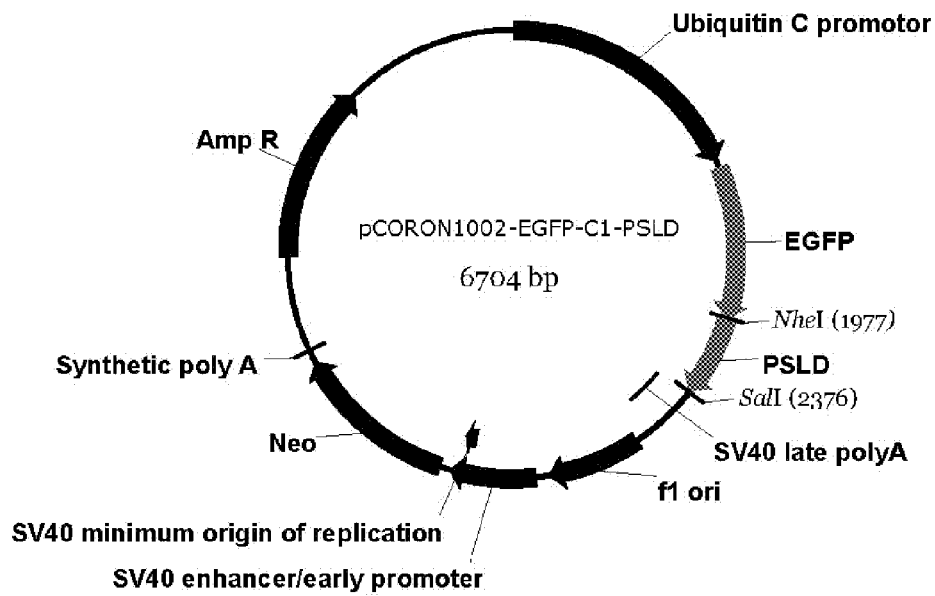

FIG. 11—Vector map of pCORON1002-EGFP-C1-PSLD.

Figure 12:
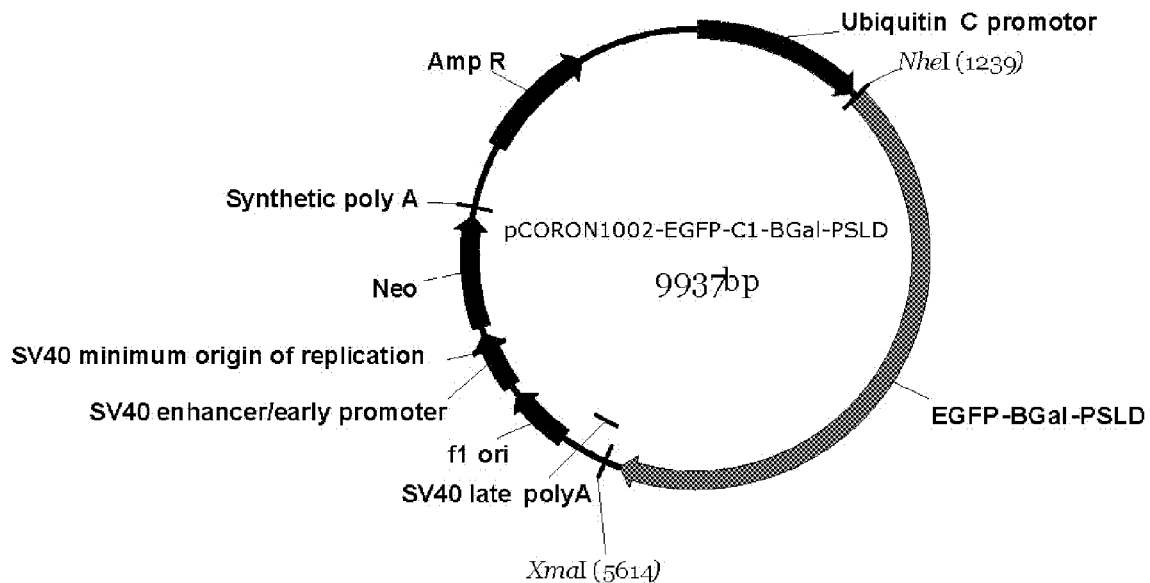

FIG. 12—Vector map of pCORON1002-EGFP-C1-βGal-PSLD

Figure 13:
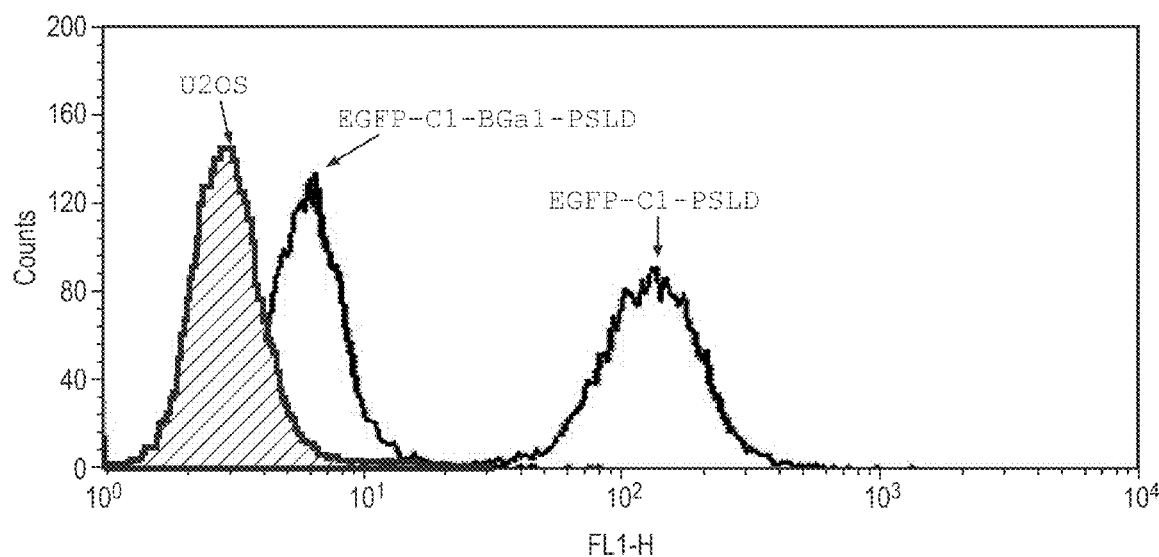

FIG. 13—Flow cytometry data comparing brightness and homogeneity of signal for representative stable cell lines developed with pCORON1002-EGFP-C1-PSLD, pCORON1002-EGFP-C1-βGal-PSLD and the parental U2OS cell line.

DETAILED DESCRIPTION OF THE INVENTION

Methods

Plasmids

PGFP-HDHB and mutant derivatives (see FIGS. 4 and 6) were created by inserting full-length HDHB cDNA as a BglII/NotI fragment (Taneja et al., J. Biol. Chem., (2002) 277, 40853-40861) into the NotI site of the pEGFP-C1 vector (Clontech, Palo Alto, Calif.). PFLAG-HDHB was constructed by inserting a HindIII/NotI fragment containing full-length HDHB cDNA into the NotI site of pFlag-CMV2 vector (Eastman Kodak Co., Rochester, N.Y.). Tagged HDHB-SLD (1-1039) was constructed by cleaving the tagged HDHB plasmid with NruI following the coding sequence for residue 1034 and with NotI in the polylinker and replacing the small fragment by a duplex adaptor oligonucleotide with a blunt end encoding residues 1035 to 1039, a stop codon, and an overhanging NotI-compatible 5' end. To create PFLAG-HDHB (1-874), StuI-digested PFLAG-HDHB DNA was treated with Klenow polymerase to generate blunt ends and ligated into the pFLAG-CMV2 vector. To generate pEGFP-βGal, a DNA fragment encoding E. coli β-galactosidase (βGal) was amplified by PCR from pβGal-control (Clontech) and inserted at the 3' end of the GFP coding sequence in pEGFP-C1, using the HindIII site. The HDHB sequence for amino acid residues 1040-1087(SLD) and 957-1087(PSLD) were PCR amplified and inserted at the 3' end of the βGal cDNA in pEGFP-βGal to create pGFP-βGal-SLD and PGFP-βGal-PSLD respectively. The NES mutants and phosphorylation site mutants were created in the HDHB cDNA by site-directed mutagenesis (QuikChange, Stratagene, La Jolla, Calif.).

pCORON1002-EGFP-C1-PSLD was constructed by PCR amplification of the 390 bp PSLD region from the DNA construct pGFP-Cl-βGal-PSLD. Introduction of 5' NheI and 3' SalI restriction enzyme sites to the PSLD fragment allowed sub-cloning into the vector pCORON1002-EGFP-C1 (GE Healthcare, Amersham, UK). The resulting 6704 bp DNA construct pCORON1002-EGFP-C1-PSLD, contains an ubiquitin C promoter, a bacterial ampicillin resistance gene and a mammalian neomycin resistance gene (FIG. 11). The nucleic acid sequence of the vector is shown in SEQ ID No. 3. Three further versions of this vector were created using standard cloning techniques (Sambrook, J. et al (1989)); the EGFP gene was first replaced with J-Red (Evrogen), the neomycin resistance gene was replaced with hygromycin resistance gene and the ubiquitin C promoter was replaced with the CMV I/E promoter.

pCORON1002-EGFP-C1-βGal-PSLD was constructed by NheI and XmaI restriction enzyme digest of pEGFP-Cl-βGal-PSLD and insertion of the 4242 bp EGFP-βGal-PSLD fragment into pCORON1002 vector (GE Healthcare). The resulting 9937 bp DNA construct PCORON 1002-EGFP-C1-βGal-PSLD (FIG. 12) contains an ubiquitin C promoter, a bacterial ampicillin resistance gene and a mammalian neomycin resistance gene. The nucleic acid sequence of the vector is shown in SEQ ID No. 4.

The protein and nucleic acid sequence for the EGFP-PSLD fusion protein are shown in SEQ ID No. 5 and 6, respectively.

The correct DNA sequence of all constructs and substitution mutations was confirmed by DNA sequencing.

Antibodies

Anti-HDHB antibody was generated against purified recombinant HDHB (Bethyl Laboratories, Montgomery, Tex.) and affinity-purified on immobilized HDHB (Harlow & Lane, Antibodies: A laboratory manual. Cold Spring Harbor Laboratory).

Cell Culture, Synchronization, Microinjection, Electroporation, Transfection and Stable Cell Line Generation U2OS cells were cultured as exponentially growing monolayers in Dulbecco-modified Eagle medium (DMEM) (Gibco BRL Lifetechnologies, Carlsbad, Calif.) supplemented with 10% fetal bovine serum (FBS) (Atlanta Biologicals, Norcross, Ga.) at 37° C. Exponentially growing U2OS cells were arrested at G1/S by incubation in DMEM containing 5 mM thymidine (Sigma-Aldrich, St. Louis, Mo.), for 24 h. To release the cells into S phase, the medium was aspirated and the cells washed three times with warm DMEM plus 10% FBS, and incubated in fresh DMEM plus 10% FBS. Exponentially growing U2OS cells were arrested in G2/M for 16 h in DMEM containing 30 ng/ml nocodazole (Sigma-Aldrich). To release cells into G1, mitotic cells were collected by gently shaking them off, washed three times with DMEM plus 10% FBS, and then plated on glass coverslips for microinjection, or in culture dishes for further manipulation.

Cell cycle synchronization was verified by flow cytometry as described previously (Taneja et al., J. Biol. Chem., (2002) 277, 40853-40861). In experiments to block nuclear protein export, cells were cultured for 3 h in DMEM containing 10 ng/ml of leptomycin B (LMB) and 10 µM cycloheximide (Calbiochem, San Diego, Calif.) to prevent new protein synthesis. Cells plated on glass coverslips were microinjected as described (Herbig et al., 1999) except that plasmid DNA rather than protein was injected.

For electroporation, asynchronously growing U2OS cells (5×106) were trypsinized, collected by centrifugation, and resuspended in 800 µl of 20 mM HEPES (pH 7.4), 0.7 mM Na2HPO4/NaH2PO4, 137 mM NaCl, 5 mM KCl, 6 mM glucose at a final pH of 7.4. Ten µg of DNA was added, transferred to a 0.4 cm electroporation cuvette (BioRad, Hercules, Calif.) and electroporation performed using Gene Pulser II apparatus (BioRad). Cells were plated in tissue culture dishes for 1 h, washed with fresh medium and cultured for another 23 h.

Working with transiently transfected cells proved difficult in multiwell plate format due to low transfection efficiency, heterogeneity of expression and problems arising from the high throughput analysis of such data. Screening for the effects of large numbers of siRNA or agents upon the cell cycle therefore required production of a homogenous stable cell line. Due to the toxic effects of HDHB when overexpressed for long periods a stable cell line was generated with the PSLD region linked to a reporter. U-2OS cells were transiently transfected with PCORON1002-EGFP-C1-PSLD (FIG. 11), PCORON1002-EGFP-C1-βGal-PSLD (FIG. 12) or J-Red derivatives of the above vectors. Stable clones expressing the recombinant fusion proteins were selected using 1 mg/ml G418 (Sigma) or hygromycin, where appropriate. Isolated primary clones (~60 per construct) were analysed by flow cytometry to confirm the level and homogeneity of expression of the sensor and where appropriate secondary clones were developed using methods above.

Fluorescence Microscopy

For indirect immunofluorescence staining, cells were washed three times with phosphate buffered saline (PBS), fixed with 3.7% formaldehyde in PBS for 20 min, permeabilized for 5 min in 0.2% Triton X-100, and incubated with 10% FBS in PBS for 45 min. FLAG-HDHB was detected with mouse monoclonal anti-FLAG antibody (Sigma-Aldrich), 1:100 in PBS plus 10% FBS for 2 h at room temperature. After washing, cells were incubated with Texas Red-conjugated goat anti-mouse secondary antibody (Jackson ImmunoResearch Laboratories, West Grove, Pa.) at 1:100 in PBS plus 10% FBS for 1 h at room temperature. After three washes, cells were incubated for 10 min with Hoechst 33258 (2 µM in PBS). Coverslips were mounted in ProLong Antifade (Molecular Probes, Eugene, Oreg.). Images were obtained with a Hamamatsu digital camera using the Openlab 3.0 software (Improvision, Lexington, Mass.) on the Zeiss Axioplan 2 Imaging system (Carl Zeiss Inc.). The number of cells that exhibited each pattern of subcellular localization was counted and expressed as a percentage of the total number of cells scored (100 to 150 cells in each experiment). The subcellular distribution of each protein was quantitatively evaluated in at least two independent experiments.

For GFP fluorescence, cells were washed three times with phosphate-buffered saline (PBS), fixed with 3.7% formaldehyde containing 2 µM Hoechst 33258 for 20 min and imaged and evaluated as above.

For Triton X-100 extraction, cells were washed twice with cold cytoskeleton buffer (CSK, 10 mM HEPES [pH 7.4], 300 mM sucrose, 100 mM NaCl, 3 mM MgCl2), and extracted for 5 min on ice with 0.5% Triton X-100 in CSK buffer (supplemented with 1× protease inhibitors) and then fixed as described above.

Where appropriate, for high throughput imaging, kinetic imaging (24 hr) and analysis in multiwell plate format of stable cell lines flourescence microscopy was conducted using a high throughput confocal imaging system (IN Cell Analyzer 1000 or IN Cell Analyzer 3000, GE Healthcare, Amersham, UK) on cells transfected with pCORON1002-EGFP-C1-PSLD, pCORON1002-EGFP-C1-βGal-PSLD or redFP derivatives of these vectors. Images were analysed using the cell cycle phase marker algorithm (GE Health Care).

Metabolic Phosphate Labeling

U2OS cells (2.5×106) were transiently transfected with wild type or mutant FLAGHDHB. After 24 h, cells were incubated in phosphate-depleted DMEM (Gibco BRL Lifetechnologies) for 15 min and radiolabeled with 32P-H3PO4 (0.35 mCi/ml of medium; ICN Pharmaceuticals Inc., Costa Mesa, Calif.) for 4 h. Phosphate-labeled FLAG-HDHB was immunoprecipitated from extracts, separated by 7.5% SDS/PAGE, and transferred to a polyvinylidene difluoride (PVDF) membrane as described below.

Cell Extracts, Immunoprecipitation, and Western Blotting

At 24 h after transfection, FLAG-HDHB-transfected cultures to be analyzed by immunoprecipitation and immunoblotting were lysed in lysis buffer (50 mM Tris-HCl pH 7.5, 10% glycerol, 0.1% NP-40, 1 mM DTT, 25 mM NaF, 100 µg/ml PMSF, 1 µg/ml aprotinin, 1 µg/ml leupeptin) (0.5 ml per 35 mm or 1 ml per 60 mm dish or 75 cm flask). The extract was scraped off the dish, incubated for 5 min on ice, and centrifuged for 10 min at 14 000 g. Samples of the supernatant (0.5 to 1 mg of protein) were incubated with 10 µl anti-FLAG agarose (Sigma) on a rotator for 2 h at 4° C. The agarose beads were washed three times with lysis buffer. Immunoprecipitated proteins were transferred to a PVDF membrane and analyzed by western blotting with anti-HDHB-peptide serum (1:5000), anti-cyclin E antibody (1:1000), and anticyclin A antibody (1:1000) (Santa Cruz Biotechnology Inc., Santa Cruz, Calif.), and chemiluminescence (SuperSignal, Pierce Biotechnology Inc., Rockford, Ill.).

For selective nuclear and cytoplasmic protein extraction, 80-90% confluent U2OS cells were harvested by trypsinization and washed with PBS. They were resuspended and lysed in 10 mM Tris-HCl [pH 7.5], 10 mM KCl, 1.5 mM MgCl2, 0.25 M sucrose, 10% glycerol, 75 µg/ml digitonin, 1 mM DTT, 10 mM NaF, 1 mM Na3VO4, 100 µg/ml PMSF, 1 µg/ml aprotinin, and 1 µg/ml leupeptin for 10 min on ice, and centrifuged at 1000×g for 5 min. The supernatant fraction was collected as the cytosolic extract. The pellet was washed, resuspended in high salt buffer (10 mM Tris-HCl [pH 7.5], 400 mM NaCl 1 mM EDTA, 1 mM EGTA, 1 mM DTT, 1% NP-40, 100 µg/ml PMSF, 1 µg/ml aprotinin, and 1 µg/ml leupeptin), and rocked for 10 min at 4° C. After sonication, the suspended material, containing both soluble and chromatin-bound protein, was analyzed as nuclear extract. Proteins in the nuclear and cytoplasmic extracts were analyzed by 8.5% SDS-PAGE, followed by western blotting with antibodies against α-tubulin, PCNA (both Santa Cruz Biotechnology), and recombinant HDHB.

Protein Phosphatase Reactions

FLAG-HDHB bound to anti-FLAG beads was incubated with 100 U of λ-phosphatase (New England Biolabs, Beverly, Mass.) in phosphatase buffer (50 mM Tris-HCl [pH 7.5], 0.1 mM EDTA, 0.01% NP-40) for 1 h at 30° C. The reaction was carried out in the presence or absence of phosphatase inhibitors (5 mM Na3VO4, 50 mM NaF). The proteins were separated by 7.5% SDSPAGE (acrylamide-bisacrylamide ratio, 30:0.36) and HDHB was detected by western blotting with anti-HDHB-peptide serum and chemiluminescence.

Tryptic Peptide Mapping and Phosphoamino Acid Analysis

At 24 h after transfection, radiolabeled FLAG-HDHB-transfected cultures to be used for immunoprecipitation and phosphoamino acid or phosphopeptide mapping were processed as above, except that lysis buffer was substituted by RIPA buffer (50 mM Tris-HCl [pH7.5], 150 mM NaCl, 1% NP-40, 0.5% deoxycholic acid, 1% SDS, 50 mM NaF, 1 mM EDTA, 5 mM Na3VO4, 100 μg/ml PMSF, 1 μg/ml aprotinin, and 1 μg/ml leupeptin). Immunoprecipitated proteins were separated by 7.5% SDS-PAGE and transferred to PVDF membranes. The membranes containing radiolabeled HDHB were rinsed well with deionized $H_2O$ twice before visualization of phosphoproteins by autoradiography. The phosphoproteins were then excised, and the membrane pieces were re-wet with methanol followed by water. The membranes were blocked with 50 mM NH4HCO3 containing 0.1% Tween 20 (Sigma-Aldrich) for 30 min at room temperature and washed three times with 50 mM NH4HCO3 before enzymatic cleavage of phosphoproteins from the PVDF with L-(tosylamido-2-phenyl) ethyl chloromethyl ketonetreated bovine pancreatic trypsin (Worthington, Lakewood, N.J.). The peptides were then subjected to two-dimensional phosphopeptide mapping or phosphoamino acid analysis as described in detail elsewhere (Boyle et al., Meth. Enzymology, (1991), 201, 110-149).

Cyclin-Dependent Kinase Reactions In Vitro

Kinase reactions using purified cyclin/CDK (200 pmol/h) (provided by R. Ott and C. Voitenleitner) and purified recombinant HDHB (Taneja et al., J. Biol. Chem., (2002) 277, 40853-40861) as the substrate were performed as described previously (Voitenleitner et al., Mol. Cell. Biol., (1999), 19, 646-56).

BrdU Labelling, Identification of Chemical Cell Cycle Blocks and RNAi Experiments on Stable Cell Lines Stable cells expressing the pCORON1002-EGFP-C1-PSLD construct, were seeded at 0.3×105/ml in 96-well Greiner plates using antibiotic-free medium (100 μl/well) and incubate for 16 hours.

To demonstrate the distribution of EGFP-PSLD in S-phase, stable cells were marked with BrdU for 1 hr using the cell proliferation kit (Amersham Biosciences, GE Health Care). Cells were fixed in 2% formalin and incorporated BrdU was detected by immunofluorescence with a Cy-5 labelled secondary antibody system (Cell proliferation kit; GE Health Care). Nulcei were stained with hoechst (2 μM).

For chemical block studies (Table 1), stable cells were exposed to olomoucine, roscovitine, nocodazole, mimosine, colcemid or colchicine (Sigma). Cells were fixed in 2% formalin and nuclei stained with hoechst (2 μM).

For siRNA studies, siRNA pools (Dharmacon) against certain cyclins, MCM proteins, CDKs, polo-like kinase (PLK), and a random control duplex (Table 2) were diluted in lipofectamine/optimem I (Invitrogen) to 25 nM and added to stable cells for 4 hrs. The medium was replaced and plates incubated for 48 hr. Cells were fixed in 2% formalin and nuclei stained with hoechst (2 μM).

After high throughput imaging and analysis on the IN Cell Analyzer system (GEHC), data for average nuclear intensity and N:C ratio (EGFP signal), nuclear size (hoescht signal) and, where appropriate, nuclear signal intensity (BrdU) were obtained for the total number of individual cells in a field of view using hoescht as a nuclear mask and the IN Cell Analyzer 3000 cell cycle phase marker algorithm (GEHC). For each well, the total number of cells per field of view were catagorised into G1-phase (predominantly nuclear EGFP distribution; high EGFP-PSLD nuclear intensity and N:C ratio), S-phase (nuclear BrdU signal >3SDs above background; EGFP-PSLD N:C ratio around 1) and G2-phase (large nuclear size; low EGFP-PSLD N:C ratio). Although it was possible to differentiate M-phase cells (based on small nuclear size and very intense EGFP signal) very few such cells were seen in wells fixed with formalin since they were removed during the washing and fixation process.

Results

HDHB Resides in Nuclear Foci or in the Cytoplasm

Figure 1:
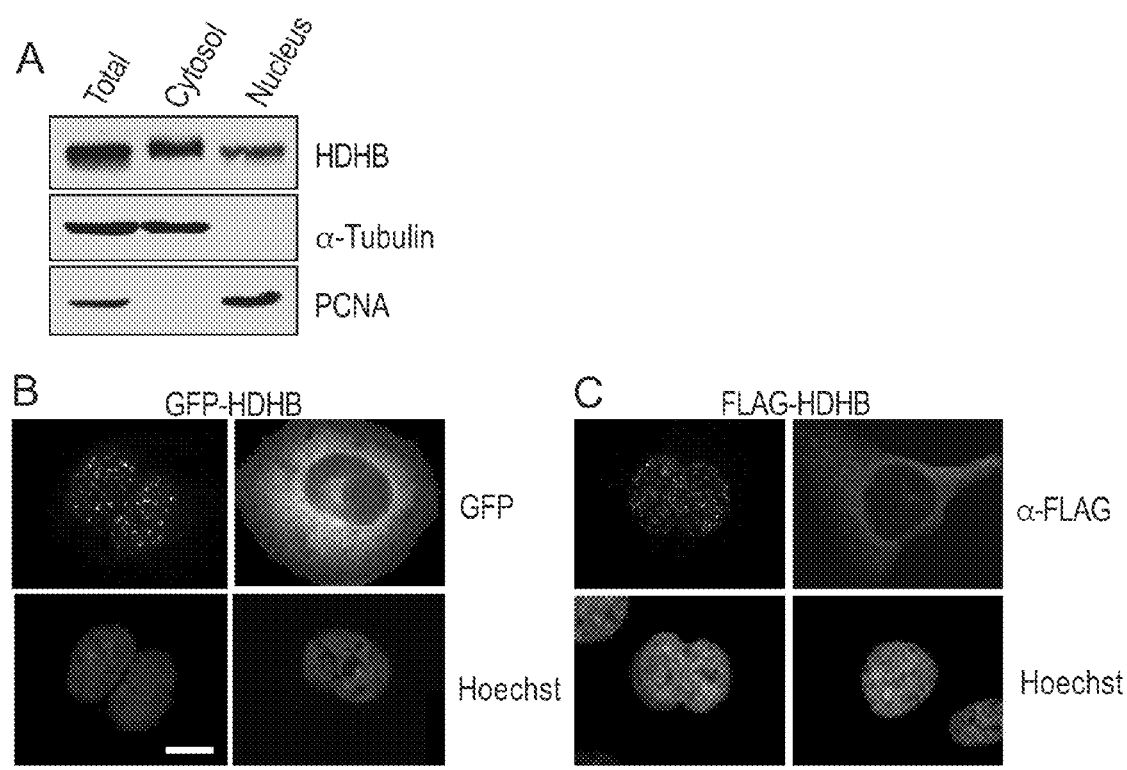
FIG. 1—Localisation of HDHB in the nucleus or cytoplasm.

To determine the subcellular localization of endogenous HDHB, nuclear and cytoplasmic proteins were selectively extracted from human U2OS cells, separated by denaturing gel electrophoresis, and analyzed by western blotting (FIG. 1). The presence of PCNA and α-tubulin in each extract was first monitored to assess the extraction procedure. PCNA was enriched in the nuclear extract and not in the cytoplasmic fraction, while α-tubulin was found primarily in the cytoplasmic fraction, validating the fractionation. HDHB was detected in both the nuclear and cytoplasmic fractions (FIG. 1). The cytoplasmic HDHB migrated more slowly than the nuclear fraction (FIG. 1), suggesting the possibility of post-translational modification.

These results could indicate either that HDHB was distributed throughout the cell, or that a mixed population of cells contained HDHB in either the nucleus or the cytoplasm. To distinguish between these alternatives, HDHB was localized in situ in single cells; GFP- and FLAG-tagged HDHB were expressed in human U2OS cells by transient transfection. Since prolonged over-expression of tagged or untagged HDHB was cytotoxic, all experiments were conducted in the shortest time period possible (usually 24 h). Tagged HDHB localization was analyzed in individual cells by fluorescence microscopy. Both GFP-HDHB and FLAG-HDHB displayed two major patterns of localization, either in the nucleus in discrete foci or in the cytoplasm (FIG. 1). GFP-HDHB transiently expressed in primary human fibroblasts was also observed in either the nucleus or the cytoplasm.

Identification of a Cell Cycle-Dependent Subcellular Localization Domain in HDHB U2OS cells were arrested in G2/M with nocodazole, released into G1 for three hours, and then microinjected with PGFP-HDHB DNA into their nuclei. GFP-HDHB expression was easily detectable six hours later, when approximately 70% of G1 phase cells had accumulated the fusion protein primarily in the nuclei (FIG. 2). In contrast, when cells were synchronized at G1/S with thymidine, released into S phase, and then microinjected with PGFP-HDHB DNA, more than 70% of S phase cells had accumulated the fusion protein predominantly in the cytoplasm (FIG. 2). Selective extraction of U2OS cells in G1 and S phase revealed that endogenous HDHB was mostly nuclear in G1 and cytoplasmic in S phase (FIG. 2b). However, endogenous HDHB was clearly detectable in both subcellular fractions. The mobility of the S phase HDHB was slightly retarded compared to the G1 phase protein. These results indicate that the subcellular localization of HDHB is regulated in the cell cycle and that GFP-tagged HDHB reflects the localization of the endogenous untagged helicase.

Prompted by the identification of C-terminal nuclear location signals in Bloom's syndrome helicase and other RecQ-family helicases (Hickson, Nature Rev. Cancer, (2003) 3, 169-178), a possible subcellular localization domain (SLD) was identified at the extreme C-terminus of HDHB (FIG. 3). To determine whether this putative SLD was important for HDHB localization, a truncation mutant of HDHB (GFP-HDHB-.SLD) was generated that lacks the C-terminal 48 residues containing the SLD (FIG. 3). The expression vector was microinjected into U2OS cells in G1 or S phase and the subcellular localization of the fusion protein was examined by fluorescence microscopy six hours later. Over 95% of the cells accumulated the fusion protein in the cytoplasm, regardless of the cell cycle timing of HDHB expression (FIG. 3c). This result suggests that HDHB may carry a NLS that is impaired or abolished by the C-terminal deletion in GFP-HDHB-ΔSLD.

To determine whether the C-terminal domain of HDHB was sufficient for nuclear localization, a bacterial β-galactosidase (βGal) was used as a reporter protein because it has a molecular mass (112 kDa) close to that of HDHB and does not contain subcellular localization signals (Kalderon et al., Cell, (1984), 39, 499-509). As a control, a GFP-βGal expression vector (FIG. 3) was created and the subcellular localization of the fusion protein monitored after microinjection of the expression vector into U2OS cells. As expected, GFP-βGal protein accumulated primarily in the cytoplasm (FIG. 4). In contrast, GFP-βGal-SLD was found in both the nucleus and cytoplasm in asynchronous or synchronized U2OS cells (FIG. 4), suggesting that SLD contains a NLS, but was not sufficient for nuclear localization of the reporter protein. Reasoning that perhaps the neighboring potential CDK phosphorylation sites might affect subcellular localization in the cell cycle (FIG. 3), a GFP-βGal-PSLD was constructed, in which the C-terminal 131 residues of HDHB, containing the putative SLD and the cluster of potential CDK phosphorylation sites, were appended to the C-terminus of GFP-βGal (FIG. 3). When the GFP-βGal-PSLD plasmid DNA was transiently expressed in asynchronous and synchronized U2OS cells, GFP-βGal-PSLD was found in the nucleus in over 90% of G1 phase cells, and in the cytoplasm in more than 70% of S phase cells (FIG. 4). In contrast with the focal pattern observed for nuclear GFP-HDHB in G1, GFP-βGal-PSLD and EGFP-PSLD proteins were distributed evenly throughout the nucleus in G1, sparing only the nucleoli. Analysis of stable cell lines expressing pCORON1002-EGFP-C1-PSLD that have been marked with BrdU emphasized that cells in S-phase (equal to approx 60% of the asychronous population) exhibit equidistribution or predominantly cytoplasmic distribution of the EGFP-PSLD signal (FIG. 10). S-phase cells do not show a predominantly nuclear distribution of EGFP-PSLD associated with G1 cells. Some cells were seen to exhibit absolute nuclear exclusion of the EGFP-PSLD reporter (FIG. 10) however these cells did not incorporate BrdU. We hypothesised that cells demonstrating absolute clearance of EGFP-PSLD from the nucleus were in G2. Kinetic imaging of the EGFP-PSLD stable cell lines over 24 hours showed that EGFP-PSLD is predominantly nuclear in G1 after mitosis, exhibits a rapid nuclear to cytoplasmic movement around the G1/S transition (~3.5 hours after cytokinesis) and further progressive translocation from the nucleus to the cytoplasm from G1/S through to the end of G2 (approx 19 hours); at this point cell rounding occurred prior to re-division. These observations seem to confirm the possibility that G2 cells exhibit an absolute cytoplasmic distribution of the EGFP-PSLD reporter. Stable expression of the EGFP-PSLD fusion was not found to affect the total length of the cell cycle (approx 24 hours) when compared to U2OS cells or the G2M cell cycle phase marker cell line (GEHC). Taken together, these data suggest that the subcellular localization of HDHB is dependent on the cell cycle, that the C-terminal PSLD domain of HDHB plays a major role in regulating the subcellular localization of the protein in a cell cycle dependent manner and that HDHB is nuclear in G1 but progressively translocates to the cytoplasm during S-phase and possibly G2.

Identification of a Functional Rev-Type NES in HDHB

A number of proteins that shuttle between the nucleus and cytoplasm have been demonstrated to contain a NES similar to the prototype NES of HIV rev protein (FIG. 5). Proteins containing a rev-type NES require the export factor CRM1 (also called exportin 1) to bind and transport proteins from the nucleus to the cytoplasm (reviewed by Weis, Cell, (2003), 112, 441-451). Leptomycin B (LMB), specifically inhibits CRM1 activity in nuclear protein export (Wolff et al., Chem. Biol., (1997), 4, 139-147; Kudo et al., Exp. Cell. Res., (1998), 242, 540-547). Inspection of the PSLD sequence in HDHB revealed a putative rev-type NES (LxxxLxxLxL; FIG. 5). To determine whether the cytoplasmic localization of HDHB requires a functional NES, expression plasmids for GFP-HDHB or FLAG-HDHB DNA were microinjected into asynchronous, G1, and S phase cells in the presence and absence of LMB. The localization of the fusion proteins was examined by fluorescence microscopy and quantified. In the presence of LMB, both fusion proteins accumulated in the nucleus independently of the cell cycle (FIG. 5), consistent with the possibility that HDHB contains a rev-type NES that functions through CRM1. However it is also possible that HDHB may not be a direct cargo of CRM1 and that its export may be indirectly mediated through some other protein(s). To assess whether the putative NES in HDHB was functional, we mutated Val/Leu and Leu/Leu of the NES motif to alanine to create NES mutants 1 and 2 (FIG. 5). GFP-HDHB and GFP-βGal-PSLD harboring these NES mutations were transiently expressed in either asynchronous or synchronized U2OS cells. Both NES mutant fusion proteins accumulated in the nucleus in more than 80% of cells, no matter when they were expressed in asynchronous or synchronized cells (FIG. 5). The results indicate that the NES mutations specifically impaired the export of both GFP-HDHB and GFP-βGal-PSLD, arguing that the PSLD region of HDHB contains a functional NES.

FLAG-HDHB is Phosphorylated in a Cell Cycle-Dependent Manner In vivo.

The cluster of potential CDK phosphorylation sites in the PSLD domain of HDHB (FIG. 3) suggested that phosphorylation of HDHB might regulate its subcellular localization in the cell cycle. If so, one would expect the PSLD region of HDHB to be phosphorylated in a cell cycle-dependent manner. To test whether HDHB undergoes phosphorylation in PSLD, U2OS cells were transiently transfected with expression plasmids for wild type and C-terminally truncated forms of FLAG-HDHB, radiolabeled with phosphate, and then FLAG-HDHB was immunoprecipitated from cell extracts. Immunoprecipitated proteins were analyzed by denaturing gel electrophoresis, immunoblotting, and autoradiography (FIG. 6). A radiolabeled band of FLAG-HDHB was detected at the same position as the immunoreactive HDHB band (FIG. 6A, lanes 1). Truncated FLAG-HDHB lacking SLD was also robustly phosphorylated in vivo (lanes 2), while truncated FLAG-HDHB (1-874) lacking PSLD was not significantly phosphorylated (lanes 3). These results demonstrate that SLD is not required for HDHB phosphorylation, while PSLD is required, and suggest that the phosphorylation sites probably reside in PSLD.

To examine the timing of HDHB phosphorylation in the cell cycle, it would be convenient to detect phosphorylation without the use of radiolabeling. Since phosphorylation often reduces the electrophoretic mobility of a protein in denaturing gels, transiently expressed FLAG-HDHB was immunoprecipitated and its mobility examined before and after treatment with λ-phosphatase (λ-PPase) (FIG. 6B). Without λ-PPase treatment, FLAG-HDHB was detected in western blots in two very closely migrating bands (lane 1), while dephosphorylated FLAG-HDHB migrated as a single band at the mobility of the faster band of the doublet (lane 2). When λ-PPase inhibitors were present in the reaction, FLAG-HDHB migrated as a doublet identical to the mock-treated protein (lane 3). These data suggest that the electrophoretic mobility of FLAG-HDHB was reduced by phosphorylation and that this assay may be suitable to track HDHB phosphorylation in the cell cycle.

To determine whether HDHB is phosphorylated in a cell cycle-dependent manner, U2OS cells transiently expressing FLAG-HDHB were arrested in G1/S by adding thymidine to the medium or in G2/M by adding nocodazole to the medium. The cells were released from the blocks for different time periods, and FLAG-HDHB was immunoprecipitated from cell extracts.

The immunoprecipitated material was incubated with or without λ-PPase and then analyzed by denaturing gel electrophoresis and western blotting (FIG. 6C). The mobility of FLAG-HDHB from cells arrested at G1/S was increased by λ-PPase treatment, suggesting that the protein was phosphorylated at G1/S (FIG. 6C, upper panel). A similar mobility shift was detected after phosphatase treatment of FLAG-HDHB for at least nine hours after release from the G1/S block (upper panel), as well as in cells arrested at G2/M (FIG. 6C, lower panel). However, after the cells were released into G1 for four and eight hours, FLAG-HDHB migrated as a single band that was much less affected by phosphatase treatment (FIG. 6C, lower panel). By twelve hours after release from the G2/M block, when most of the cells were entering S phase (data not shown), the mobility of FLAG-HDHB was again increased by phosphatase treatment, restoring the pattern observed in nocodazole-arrested cells (lower panel). These results strongly suggest that phosphorylation of FLAG-HDHB is cell cycle-dependent, with maximal phosphorylation from G1/S through G2/M and minimal phosphorylation during G1.

Serine 967 is the Major Phosphorylation Site of Ectopically Expressed HDHB.

To map the phosphorylation sites in FLAG-HDHB, we first wished to determine what amino acid residues were modified. Phosphoamino acid analysis of in vivo radiolabeled FLAG-HDHB revealed that phosphoserine(s) was the major phosphoamino acid of FLAG-HDHB in vivo (FIG. 7A). Assuming that the cell cycle-dependent phosphorylation sites of HDHB are located in PSLD between residues 874 and 1039 (FIG. 3A), that these sites are modified by CDKs, and that phosphoserine is the major amino acid modified (FIG. 7A), only four of the seven potential CDK sites would remain as candidate sites. To test each of these sites individually, FLAG-HDHB expression plasmids with the corresponding serine to alanine mutations were constructed. Cells transiently transfected with these plasmids were radiolabeled with orthophosphate in vivo and FLAG-HDHB was immunoprecipitated and analyzed by autoradiography and western blotting (FIG. 7B). The results showed that FLAG-HDHB and three of the mutant proteins were phosphorylated approximately equally, while the S967A mutant protein was only weakly phosphorylated (FIG. 7B). This result suggested that S967 might be the primary site of HDHB phosphorylation in vivo. Consistent with this interpretation, an electrophoretic mobility shift after phosphatase treatment of immunoprecipitated FLAG-HDHB was detected with three of the mutant proteins, but not with S967A protein.

To confirm that S967 was the major phosphorylation site in HDHB in vivo, tryptic phosphopeptide mapping was carried out with wild type and S967A mutant FLAG-HDHB that had been metabolically radiolabeled with orthophosphate (FIG. 7C). One predominant radiolabeled peptide and a weakly labeled peptide were observed with the wild type protein (left panel). The predominant phosphopeptide was absent in the S967A protein, but the weakly labeled peptide remained detectable (FIG. 7C, right panel). The results provide additional evidence that serine 967 is a prominent phosphorylation site in HDHB in vivo.

Identification of Cyclin E/CDK2 as a Kinase that Potentially Modifies HDHB in G1/S To test whether CDKs can actually modify HDHB, as suggested by the timing of HDHB phosphorylation in the cell cycle and the identification of S967 as a primary site of modification, purified cyclin E/CDK2 or cyclin A/CDK2 were incubated with purified recombinant HDHB and radiolabeled ATP in vitro. After the kinase reactions, the proteins were separated by denaturing gel electrophoresis, transferred to a PVDF membrane, and detected by autoradiography. The results revealed that recombinant HDHB could be phosphorylated strongly by both cyclin E/CDK2 and cyclin A/CDK2. The radiolabeled HDHB bands were then further processed for tryptic phosphopeptide mapping. Peptides from each digestion were separated in two dimensions, either individually or after mixing with tryptic peptides from in vivo phosphorylated FLAG-HDHB, and visualized by autoradiography (FIG. 8A). HDHB peptides phosphorylated by cyclin E/CDK2 and cyclin A/CDK2 yielded patterns essentially identical to those observed in the in vivo labeled peptide map, with one major spot and one minor spot (FIG. 8A). When the in vitro and in vivo labeled peptides were mixed and separated on one chromatogram, they co-migrated (FIG. 8A, right). These data argue that the major phosphopeptides modified in vitro by cyclin E/CDK2 and cyclin A/CDK2 in purified recombinant HDHB were the same ones modified in vivo in FLAG-HDHB.

Since cyclin E activity in human cells rises in late G1, while cyclin A activity rises later coincident with the onset of S phase (Pines, 1999; Erlandsson et al., 2000), it was important to try to distinguish whether one of these kinases might preferentially modify HDHB. Cyclin subunits frequently form a complex with the substrate proteins that they target for phosphorylation (Endicott et al., 1999; Takeda et al., 2001). To test whether cyclin E or cyclin A could associate with HDHB, FLAG-HDHB and associated proteins were immunoprecipitated from extracts of cells transfected with either FLAG-HDHB expression vector or empty FLAG vector as a control. The cell extracts and the immunoprecipitated material were analyzed by western blotting (FIG. 8B). Cyclin E clearly co-precipitated with FLAG-HDHB, but cyclin A did not (FIG. 8B, lanes 2 and 5), suggesting that FLAG-HDHB may interact preferentially with cyclin E in vivo. It is conceivable that this interaction may be required for phosphorylation of HDHB by cyclin E/CDK2 in vivo, and if so, mutations in HDHB that prevent its association with cyclin E would abrogate phosphorylation by cyclin E/CDK2. To test the possibility that the FLAG-HDHB mutant S967A was not phosphorylated in vivo (FIG. 7B, C) due to an inability to bind to cyclin E, FLAG-HDHB-S967A and associated proteins were immunoprecipitated from extracts of transfected cells and analyzed by western blotting. Co-precipitation of cyclin E with the mutant protein was as robust as with wild type FLAG-HDHB.

Phosphorylation of Serine 967 is Critical for Regulation of HDHB Localization.

The data above indicate that subcellular localization and phosphorylation of ectopically expressed HDHB were regulated in a cell cycle-dependent manner with maximal phosphorylation from G1/S to G2/M, coinciding with the period when HDHB accumulated in the cytoplasm. These results, together with the identification of S967 as the major in vivo phosphorylation site in HDHB, suggest that phosphorylation of S967 may regulate the subcellular localization of HDHB. To test this idea, expression plasmids for wild type GFP-HDHB and the mutants S967A, S984A, S1005A, and S1021A were microinjected into synchronized U2OS cells. Wild type GFP-HDHB accumulated in nuclear foci of cells in G1, but in the cytoplasm of cells in S phase as expected. However, regardless of cell cycle timing, GFP-HDHB-S967A localized in nuclear foci in about 70% of the fluorescent cells (FIG. 9). The other three substitution mutants localized in either the nucleus or the cytoplasm like wild type GFP-HDHB. In an attempt to mimic the phosphorylation of S967, serine 967 was mutated to aspartic acid, GFP-HDHB-S967D was expressed in asynchronous and synchronized U2OS cells, and the subcellular distribution of the mutant fusion protein was examined.

About 60% of the cells expressing GFP-HDHB-S967D displayed cytoplasmic fluorescence in asynchronous, G1 phase, and S phase cells (FIG. 9A), demonstrating that the S967D mutation mimicked phosphorylated S967. The data strongly suggest that phosphorylation of serine 967 is critical in regulating the subcellular localization of HDHB.

A C-Terminal Domain of HDHB Confers Cell Cycle-Dependent Localization

A 131-residue domain, PSLD, is sufficient to target HDHB, EGFP or a βGal reporter to either the nucleus or the cytoplasm in a cell cycle-dependent manner (FIGS. 4 and 10). A rev-type NES resides in this domain (FIG. 5), but its activity or accessibility to the nuclear export machinery depends on phosphorylation of PSLD, primarily on serine 967, at the G1/S transition (FIG. 6-9). S967 is a perfect match to the consensus CDK substrate recognition motif (S/T)PX(K/R). Both cyclin E/CDK2 and cyclin A/CDK2 can modify HDHB in vitro, but the ability of cyclin E/CDK2 to complex with HDHB in cell extracts suggests that it may be the initial kinase that modifies HDHB at the G1/S transition (FIG. 8). Addition of olomoucine and roscovitin, known Cdk2 inhibitors (Table 1), or siRNA toward cyclin E (Table 2) resulted in predominantly nuclear distribution of EGFP-PSLD and arrest in G1 for EGFP-PSLD stable cell lines, further supporting the possibility that Cdk2/cyclin E is responsible for control of the observed cell-cycle based phosphorylation-dependent subcellular localisation. Phosphorylation of PSLD appears to persist through the latter part of the cell cycle, correlating well with the predominantly cytoplasmic localization of HDHB in S and G2. Kinetic imaging of stable cell lines treated with olomoucine over 24 hours showed that, for cells arrested in G2 the EGFP-PSLD signal redistributes from the cytoplasm to the nucleus over ~4-8 hours (without the cell passing through mitosis) suggesting that in the absence of cdk2 activity the EGFP-PSLD either becomes dephosphorylated and re-enters the nucleus, or is destroyed and newly synthesised protein is not phosphorylated due to cdk2 inhibition and therefore locates in the nucleus.

TABLE 1

| Compound | % S | G1 | G2 | Total cells |
|---|---|---|---|---|
| Colcemid (0.3 μM) | 41 | 16 | 43 | 490 |
| Colcemid (1.2 μM) | 32 | 8 | 59 | 450 |
| Colchicine (4 μM) | 36 | 9 | 55 | 467 |
| Colchicine (100 μM) | 32 | 12 | 57 | 439 |
| L-mimosine (2 mM) | 68 | 6 | 26 | 1710 |
| Olomoucine (500 μM) | 33 | 63 | 4 | 600 |
| Roscovitin (100 μM) | 36 | 52 | 13 | 693 |
| Nocodazole (3 μM) | 33 | 6 | 61 | 606 |
| Control | 61 | 17 | 22 | 2137 |

TABLE 2

| siRNA | % S | G1 | G2 | Total cells |
|---|---|---|---|---|
| PLK | 53 | 9 | 38 | 66 |
| MCM7 | 58 | 13 | 29 | 231 |
| MCM6 | 64 | 14 | 22 | 166 |
| MCM5 | 63 | 17 | 20 | 260 |
| MCM4 | 56 | 20 | 24 | 223 |
| MCM3 | 59 | 23 | 19 | 188 |
| MCM2 | 50 | 24 | 26 | 266 |
| Cyclin B1 V2 | 49 | 36 | 15 | 280 |
| Cyclin B1 V1 | 60 | 24 | 17 | 203 |
| CDK8 | 50 | 23 | 27 | 299 |
| CDK7 | 56 | 18 | 26 | 354 |
| CDK6 | 58 | 22 | 20 | 328 |
| Cyclin A2 | 61 | 13 | 26 | 319 |
| Cyclin A1 | 66 | 10 | 24 | 298 |
| Cyclin T2b | 57 | 12 | 31 | 267 |
| Cyclin T2b | 55 | 22 | 23 | 355 |
| cyclinT1 | 60 | 20 | 20 | 260 |
| cyclinE1 | 49 | 27 | 24 | 272 |
| Control | 69 | 10 | 20 | 262 |

It was not possible to distinguish whether HDHB undergoes dephosphorylation at the M/G1 transition (FIG. 6C) or is perhaps targeted for proteolysis and rapidly re-synthesized in early G1, when it would enter the nucleus. However, kinetic imaging of stable cell lines over 24 hours showed that the EGFP-PSLD signal is not greatly reduced during M phase or at the M/G1 boundary, but becomes predominantly nuclear approximately 30 minutes after cytokinesis (this state then persists for ~3 hours during G1), coincident with nuclear membrane formation. This indicates that the EGFP-PSLD construct is dephosphorylated rather than undergoing significant destruction around the M/G1 boundary.

These data provide strong evidence that the PSLD contains active targeting signals that are independent of protein context (FIG. 2-5, 10). Since mutant HDHB with an inactivated NES is nuclear even when it is expressed during S phase and thus presumably phosphorylated (FIG. 5), it is probable that the NLS is not inactivated by phosphorylation and that the primary target of CDK regulation is the NES. Extending this reasoning, the NES may be masked during G1 when the CDK motifs in PSLD are unmodified, and that the NES is liberated when S967 becomes phosphorylated, leading to NES recognition by nuclear export factors (FIG. 3-5). Structural studies of a rev-type NES have shown that it forms an amphipathic α-helix, with the leucines aligned on one side of the helix and charged residues on the other side (Rittinger et al., Mol. Cell. Biol. (1999), 4, 153-166). Since the SLD of HDHB contains both the rev-type NES and an NLS, and the basic residues likely to serve as the NLS are interspersed through the NES, the NES and NLS may reside on opposite faces of an amphipathic helix. Additional sequences in PSLD would mask the NES intramolecularly, allowing only the NLS to be recognized. Phosphorylation of S967 would alter the conformation of the mask in PSLD to expose the NES, without affecting exposure of the NLS.

High throughput Screening for Inhibitors of the Cell Cycle with EGFP-PSLD Stable Cell Lines As stated above, working with transiently transfected cells proved difficult in multiwell plate format due to low transfection efficiency, heterogeneity of expression and problems arising from the high throughput analysis of such data. Screening for the effects of large numbers of siRNA or agents upon the cell cycle therefore required production of a homogenous stable cell line. A stable cell line was generated with the PSLD region linked to a reporter (EGFP) via a flexible seven amino acid linker (using pCORON1002-EGFP-C1-PSLD). As can be seen from FIG. 13, the fluorescent signal generated by the stable cell lines developed with PCORON 1002-EGFP-C1-βGal-PSLD was significantly smaller (approximately ten-fold) than that produced by cells lines having the flexible seven amino acid linker. This is probably due to the size of the βGal protein placing large demands upon the transcriptional and translational machinery of the cell.

A stable cell line developed with PCORON1002-EGFP-C1-PSLD (see FIG. 13) was homogeneous (average total cell RFU 435, SD 58; n=271; see FIG. 10) in nature and provided sensitive, stable and uniform assays for investigating the cell cycle and for rapidly screening the effect of agents upon the cell cycle in multiwell plate format (Tables 1 and 2; and FIG. 10).

Certain aspects of the invention disclosed hereinabove has been published in Molecular Biology of the Cell (15: 3320-3332, July 2004) and electronically published as MBC in press, 10.1091/mbc.E04-03-0227 on May 14, 2004, under the title of "Cell Cycle-dependent Regulation of a Human DNA Helicase That Localizes in DNA Damage Foci", the disclosure of which is incorporated herein by reference in its entireties.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

What is claimed is:

1. An isolated nucleic acid construct encoding a polypeptide construct which comprises a detectable live-cell reporter molecule linked via a polypeptide group having a molecular mass of less than 1,000 Daltons to another polypeptide consisting of amino acid sequence 957-1087 of SEQ ID NO:1, which amino acid sequence is the phosphorylation-dependent subcellular localization domain of the C-terminal special control region of helicase B (PSLD), wherein the translocation of said construct within a mammalian cell is indicative of the cell cycle position.

2. The nucleic acid construct of claim 1, wherein said construct additionally comprises and is operably linked to and under the control of at least one cell cycle independent expression control element.

3. The nucleic acid construct of claim 2, wherein said expression control element is either an ubiquitin C promoter or a CMV promoter.

4. The nucleic acid construct of claim 1, comprising a CMV promoter, and sequences encoding PSLD and EGFP or J-Red.

5. The nucleic acid construct of claim 1, comprising a ubiquitin C promoter, and sequences encoding PSLD and EGFP or J-Red.

6. A vector comprising the nucleic acid construct of claim 1.

7. A vector according to claim 6, wherein said vector is either a viral vector or a plasmid.

8. A vector according to claim 7, wherein said viral vector is an adenoviral vector or a lentiviral vector.

9. An isolated host cell transfected with the nucleic acid construct of claim 1.

10. The host cell according to claim 9, wherein said cell is a human cell.

11. A stable cell line comprising one or more of the host cells of claim 9.

12. The nucleic acid construct of claim 1, wherein said polypeptide group has a molecular mass of less than 700 Daltons.

13. The nucleic acid construct of claim 1, wherein said polypeptide group has a molecular mass of less than 500 Daltons.

14. The nucleic acid construct of claim 1, wherein said polypeptide group is a heptapeptide.

15. The nucleic acid construct of claim 14, wherein said heptapeptide is Glycine-Asparagine-Glycine-Glycine-Asparagine-Alanine-Serine (SEQ ID NO:18).

16. The nucleic acid construct of claim 1, wherein the live-cell reporter molecule is selected from the group consisting of fluorescent protein, enzyme reporter and antigenic tag.

17. The nucleic acid construct of claim 16, wherein said fluorescent protein is selected from the group consisting of Green Fluorescent Protein (GFP), Enhanced Green Fluorescent Protein (EGFP), Emerald and J-Red.

* * * * *

SEQUENCE LISTING

<160> NUMBER OF SEQ ID NOS: 18

<210> SEQ ID NO 1
<211> LENGTH: 3264
<212> TYPE: DNA
<213> ORGANISM: Homo sapiens

<400> SEQUENCE: 1

```
atggccaggt cgagtccgta cctgcgccaa cttcagggac ctctgctccc acccagggat      60
ctggtggagg aggacgacga ctacctaaac gacgacgtgg aggaggatga agagtccgtg     120
ttcatcgacg ccgaggagct ctgcagtggg ggcgtaaagg ctggcagcct ccccgggtgc     180
ctccgcgttt ctatttgtga tgaaaacaca caagagacat gtaaagtgtt tggacgtttt     240
ccgataacag gtgcttggtg gagagtgaag gtacaagtaa agcctgtggt gggatcaagg     300
agctatcaat atcaagttca aggatttccg tcttactttt tgcagtctga tatgtcacca     360
ccaaatcaaa aacatatctg tgctctcttt cttaaagagt gtgaggtctc cagtgatgat     420
gttaataaat ttttaacatg ggtaaaggag gtatcaaact acaaaaacct aaactttgaa     480
aatcttaggg aaacactaag aactttccac aaggaaactg gaaggaaaga tcaaaagcag     540
cctacacaga atggtcagga agagttgttc ctagacaatg agatgagtct tcctctggaa     600
aacacaattc catttagaaa tgtaatgaca gctttgcagt ttccgaagat aatggaattc     660
```

```
cttccagttc ttctgcctcg acactttaaa tggatcatag ggtcaggttc taaagagatg    720
ttgaaagaga tagaagagat tttaggtaca catccgtgga aacttggatt tagtaaaata    780
acctacagag agtggaaact cctgcgatgt gaggcaagtt ggatagcatt ttgtcagtgt    840
gagtctcttc tccagctgat gactgatttg gagaagaatg cattaataat gtattccaga    900
ctgaagcaga tatgtagaga agatgggcac acatatgttg aagtgaatga cttaactttg    960
acattgtcaa atcatatgtc atttcatgct gcttcagagt ctctgaagtt tttgaaggat   1020
attggtgtgg tgacatatga gaagtcctgt gtcttccctt atgaccttta ccatgctgaa   1080
agagccatcg cctttcaat ttgtgacctg atgaagaaac ctccttggca tttatgtgtc    1140
gatgtcgaaa aggtgcttgc ctctattcac accacaaaac ctgagaattc aagcgatgat   1200
gcattgaatg agagcaaacc tgatgaagta agattagaaa atcctgtgga tgttgtggac   1260
acacaggaca atggtgacca tatttggact aatggtgaaa atgaaattaa tgcagaaata   1320
agtgaagttc agctggatca ggatcaggtt gaagttccac tggatcggga tcaggtggct   1380
gctttggaaa tgatttgctc caatcctgtg acagtcataa gtgggaaagg tggatgtggg   1440
aagaccacaa tcgttagccg tctttttaag catatagagc agttggaaga agagaagta    1500 aaaaaagcct gtgaagattt tgaacaagac cagaatgctt cagaagaatg gattaccttt   1560
actgagcaaa gtcaactaga ggcggacaag gctatagaag ttttgctcac agcacctaca   1620
gggaaagcag ctggcttact aagacagaaa actggtcttc atgcctacac actgtgtcag   1680
gtcaattata gcttctattc atggactcaa acaatgatga ccacaaacaa accatggaaa   1740
ttttcttcgg ttagagttct ggttgtggat gaagggagtt tggtatctgt aggaatcttc   1800
aaatcggtct taaatttatt gtgtgagcac tccaaacttt ctaagcttat tatccttggt   1860
gacattagac agttacccag tattgaacct ggtaacttgc tgaaagatct ttttgagact   1920
cttaagtcaa gaaattgtgc tattgagcta aagacaaacc atagagcaga atctcagctc   1980
attgtggaca atgctacaag aatctcaaga cgccaatttc caaaatttga tgcagaacta   2040
aatatctctg ataatccaac attacccatc tcaattcaag ataagacatt tattttgtc    2100 aggctcccag aagaggatgc cagttctcag tcatctaaaa ctaatcatca ctcttgttta   2160
tattctgcag ttaaaacttt actacaagaa aataacttac aaaatgcaaa acatcacaa    2220 tttattgcat ttagaaggca agactgtgat ctaattaatg actgctgctg caaacactac   2280
acaggccacc tcaccaaaga ccatcagagt agacttgttt ttggaattgg tgataaaatt   2340
tgttgtacca ggaatgcata cctctcagac ttactacctg aaaatatctc tggaagtcag   2400
caaaataatg atctagatgc cagtagtgaa gacttttctg gtacgcttcc tgattttgct   2460
aaaaataagc gtgactttga agtaacgttc gactgtgca atggagagat atttttcata   2520
acaaatgatg taactgatgt aacttttgga aagagaagat ctttgaccat taataatatg   2580
gctggcctgg aagtaactgt ggattttaag aaactaatga atattgtcg cataaaacat   2640 gcatgggcaa gaactattca cacttttcag gggtccgagg agcaaacagt tgtctatgtg   2700 gtgggggaagg cgggccgcca gcactggcag catgtctaca ccgccgtgac caggggccgc   2760
tgccgagtgt atgtgattgc agaggagtct cagctccgga atgccattat gaaaaacagt   2820
tttcctagaa aaactcgttt gaaacatttc ttgcaaagta agctctcctc tagcggcgca   2880
cctccagcag attttccgtc cccacggaag agctctggag acagtggagg acccagcaca   2940
ccgtcagcat ctcccactcc ctgtagtcaca gaccacgcca tgacaaatga tgtcacctgg   3000
agcgaggcct cttcgcctga tgagaggaca ctcacctttg ctgaaagatg gcaattatct   3060
```

-continued

```
tcacctgatg gagtagatac agatgatgat ttaccaaaat cgcgagcatc caaaagaacc   3120
tgtggtgtga atgatgatga agtccaagc aaaattttta tggtgggaga atctccacaa   3180
gtgtcttcca gacttcagaa tttgagactg aataatttaa ttcccaggca acttttcaag   3240
cccaccgata atcaagaaac ttag                                           3264
```

<210> SEQ ID NO 2
<211> LENGTH: 1087
<212> TYPE: PRT
<213> ORGANISM: Homo sapiens

<400> SEQUENCE: 2

```
Met Ala Arg Ser Ser Pro Tyr Leu Arg Gln Leu Gln Gly Pro Leu Leu
1               5                   10                  15

Pro Pro Arg Asp Leu Val Glu Glu Asp Asp Tyr Leu Asn Asp Asp
            20                  25                  30

Val Glu Asp Glu Glu Ser Val Phe Ile Asp Ala Glu Leu Cys
        35                  40                  45

Ser Gly Gly Val Lys Ala Gly Ser Leu Pro Gly Cys Leu Arg Val Ser
    50                  55                  60

Ile Cys Asp Glu Asn Thr Gln Glu Thr Cys Lys Val Phe Gly Arg Phe
65                  70                  75                  80

Pro Ile Thr Gly Ala Trp Trp Arg Val Lys Val Gln Val Lys Pro Val
                85                  90                  95

Val Gly Ser Arg Ser Tyr Gln Tyr Gln Val Gln Gly Phe Pro Ser Tyr
            100                 105                 110

Phe Leu Gln Ser Asp Met Ser Pro Pro Asn Gln Lys His Ile Cys Ala
        115                 120                 125

Leu Phe Leu Lys Glu Cys Glu Val Ser Ser Asp Asp Val Asn Lys Phe
    130                 135                 140

Leu Thr Trp Val Lys Glu Val Ser Asn Tyr Lys Asn Leu Asn Phe Glu
145                 150                 155                 160

Asn Leu Arg Glu Thr Leu Arg Thr Phe His Lys Glu Thr Gly Arg Lys
                165                 170                 175

Asp Gln Lys Gln Pro Thr Gln Asn Gly Gln Glu Glu Leu Phe Leu Asp
            180                 185                 190

Asn Glu Met Ser Leu Pro Leu Glu Asn Thr Ile Pro Phe Arg Asn Val
        195                 200                 205

Met Thr Ala Leu Gln Phe Pro Lys Ile Met Glu Phe Leu Pro Val Leu
    210                 215                 220

Leu Pro Arg His Phe Lys Trp Ile Ile Gly Ser Gly Ser Lys Glu Met
225                 230                 235                 240

Leu Lys Glu Ile Glu Glu Ile Leu Gly Thr His Pro Trp Lys Leu Gly
                245                 250                 255

Phe Ser Lys Ile Thr Tyr Arg Glu Trp Lys Leu Leu Arg Cys Glu Ala
            260                 265                 270

Ser Trp Ile Ala Phe Cys Gln Cys Glu Ser Leu Leu Gln Leu Met Thr
        275                 280                 285

Asp Leu Glu Lys Asn Ala Leu Ile Met Tyr Ser Arg Leu Lys Gln Ile
    290                 295                 300

Cys Arg Glu Asp Gly His Thr Tyr Val Glu Val Asn Asp Leu Thr Leu
305                 310                 315                 320

Thr Leu Ser Asn His Met Ser Phe His Ala Ala Ser Glu Ser Leu Lys
                325                 330                 335
```

-continued

```
Phe Leu Lys Asp Ile Gly Val Val Thr Tyr Glu Lys Ser Cys Val Phe
            340                 345                 350

Pro Tyr Asp Leu Tyr His Ala Glu Arg Ala Ile Ala Phe Ser Ile Cys
            355                 360                 365

Asp Leu Met Lys Pro Pro Trp His Leu Cys Val Asp Val Glu Lys
            370                 375                 380

Val Leu Ala Ser Ile His Thr Thr Lys Pro Glu Asn Ser Ser Asp Asp
385                 390                 395                 400

Ala Leu Asn Glu Ser Lys Pro Asp Glu Val Arg Leu Glu Asn Pro Val
                405                 410                 415

Asp Val Val Asp Thr Gln Asp Asn Gly Asp His Ile Trp Thr Asn Gly
            420                 425                 430

Glu Asn Glu Ile Asn Ala Glu Ile Ser Glu Val Gln Leu Asp Gln Asp
            435                 440                 445

Gln Val Glu Val Pro Leu Asp Arg Asp Gln Val Ala Ala Leu Glu Met
            450                 455                 460

Ile Cys Ser Asn Pro Val Thr Val Ile Ser Gly Lys Gly Gly Cys Gly
465                 470                 475                 480

Lys Thr Thr Ile Val Ser Arg Leu Phe Lys His Ile Glu Gln Leu Glu
                485                 490                 495

Glu Arg Glu Val Lys Lys Ala Cys Glu Asp Phe Glu Gln Asp Gln Asn
            500                 505                 510

Ala Ser Glu Glu Trp Ile Thr Phe Thr Glu Gln Ser Gln Leu Glu Ala
            515                 520                 525

Asp Lys Ala Ile Glu Val Leu Leu Thr Ala Pro Thr Gly Lys Ala Ala
            530                 535                 540

Gly Leu Leu Arg Gln Lys Thr Gly Leu His Ala Tyr Thr Leu Cys Gln
545                 550                 555                 560

Val Asn Tyr Ser Phe Tyr Ser Trp Thr Gln Thr Met Met Thr Thr Asn
                565                 570                 575

Lys Pro Trp Lys Phe Ser Ser Val Arg Val Leu Val Val Asp Glu Gly
            580                 585                 590

Ser Leu Val Ser Val Gly Ile Phe Lys Ser Val Leu Asn Leu Leu Cys
            595                 600                 605

Glu His Ser Lys Leu Ser Lys Leu Ile Ile Leu Gly Asp Ile Arg Gln
            610                 615                 620

Leu Pro Ser Ile Glu Pro Gly Asn Leu Leu Lys Asp Leu Phe Glu Thr
625                 630                 635                 640

Leu Lys Ser Arg Asn Cys Ala Ile Glu Leu Lys Thr Asn His Arg Ala
                645                 650                 655

Glu Ser Gln Leu Ile Val Asp Asn Ala Thr Arg Ile Ser Arg Arg Gln
            660                 665                 670

Phe Pro Lys Phe Asp Ala Glu Leu Asn Ile Ser Asp Asn Pro Thr Leu
            675                 680                 685

Pro Ile Ser Ile Gln Asp Lys Thr Phe Ile Phe Val Arg Leu Pro Glu
            690                 695                 700

Glu Asp Ala Ser Ser Gln Ser Ser Lys Thr Asn His His Ser Cys Leu
705                 710                 715                 720

Tyr Ser Ala Val Lys Thr Leu Leu Gln Glu Asn Asn Leu Gln Asn Ala
                725                 730                 735

Lys Thr Ser Gln Phe Ile Ala Phe Arg Arg Gln Asp Cys Asp Leu Ile
            740                 745                 750
```

```
Asn Asp Cys Cys Cys Lys His Tyr Thr Gly His Leu Thr Lys Asp His
        755                 760                 765
Gln Ser Arg Leu Val Phe Gly Ile Gly Asp Lys Ile Cys Cys Thr Arg
        770                 775                 780
Asn Ala Tyr Leu Ser Asp Leu Leu Pro Glu Asn Ile Ser Gly Ser Gln
785                 790                 795                 800
Gln Asn Asn Asp Leu Asp Ala Ser Ser Glu Asp Phe Ser Gly Thr Leu
                805                 810                 815
Pro Asp Phe Ala Lys Asn Lys Arg Asp Phe Glu Ser Asn Val Arg Leu
                820                 825                 830
Cys Asn Gly Glu Ile Phe Phe Ile Thr Asn Asp Val Thr Asp Val Thr
                835                 840                 845
Phe Gly Lys Arg Arg Ser Leu Thr Ile Asn Asn Met Ala Gly Leu Glu
                850                 855                 860
Val Thr Val Asp Phe Lys Lys Leu Met Lys Tyr Cys Arg Ile Lys His
865                 870                 875                 880
Ala Trp Ala Arg Thr Ile His Thr Phe Gln Gly Ser Glu Glu Gln Thr
                885                 890                 895
Val Val Tyr Val Val Gly Lys Ala Gly Arg Gln His Trp Gln His Val
                900                 905                 910
Tyr Thr Ala Val Thr Arg Gly Arg Cys Arg Val Tyr Val Ile Ala Glu
                915                 920                 925
Glu Ser Gln Leu Arg Asn Ala Ile Met Lys Asn Ser Phe Pro Arg Lys
            930                 935                 940
Thr Arg Leu Lys His Phe Leu Gln Ser Lys Leu Ser Ser Ser Gly Ala
945                 950                 955                 960
Pro Pro Ala Asp Phe Pro Ser Pro Arg Lys Ser Ser Gly Asp Ser Gly
                965                 970                 975
Gly Pro Ser Thr Pro Ser Ala Ser Pro Leu Pro Val Val Thr Asp His
                980                 985                 990
Ala Met Thr Asn Asp Val Thr Trp Ser Glu Ala Ser Ser Pro Asp Glu
        995                 1000                1005
Arg Thr Leu Thr Phe Ala Glu Arg Trp Gln Leu Ser Ser Pro Asp
        1010                1015                1020
Gly Val Asp Thr Asp Asp Leu Pro Lys Ser Arg Ala Ser Lys
        1025                1030                1035
Arg Thr Cys Gly Val Asn Asp Asp Glu Ser Pro Ser Lys Ile Phe
        1040                1045                1050
Met Val Gly Glu Ser Pro Gln Val Ser Ser Arg Leu Gln Asn Leu
        1055                1060                1065
Arg Leu Asn Asn Leu Ile Pro Arg Gln Leu Phe Lys Pro Thr Asp
        1070                1075                1080
Asn Gln Glu Thr
        1085

<210> SEQ ID NO 3
<211> LENGTH: 6704
<212> TYPE: DNA
<213> ORGANISM: Artificial Sequence
<220> FEATURE:
<223> OTHER INFORMATION: pCORON1002-EGFP-C1-PSLD

<400> SEQUENCE: 3
ggcctccgcg ccgggttttg gcgcctcccg cgggcgcccc cctcctcacg gcgagcgctg      60
ccacgtcaga cgaagggcgc agcgagcgtc ctgatccttc cgcccggacg ctcaggacag     120
```

-continued

```
cggcccgctg ctcataagac tcggccttag aaccccagta tcagcagaag gacattttag      180
gacgggactt gggtgactct agggcactgg ttttctttcc agagagcgga acaggcgagg      240
aaaagtagtc ccttctcggc gattctgcgg agggatctcc gtggggcggt gaacgccgat      300
gattatataa ggacgcgccg ggtgtggcac agctagttcc gtcgcagccg ggatttgggt      360
cgcggttctt gtttgtggat cgctgtgatc gtcacttggt gagtagcggg ctgctgggct      420
ggccggggct ttcgtggccg ccgggccgct cggtgggacg gaagcgtgtg gagagaccgc      480
caagggctgt agtctgggtc cgcgagcaag gttgccctga actgggggtt gggggggagcg     540 cagcaaaatg gcggctgttc ccgagtcttg aatggaagac gcttgtgagg cgggctgtga      600
ggtcgttgaa acaaggtggg gggcatggtg ggcggcaaga acccaaggtc ttgaggcctt      660
cgctaatgcg ggaaagctct tattcgggtg agatgggctg gggcaccatc tggggaccct      720
gacgtgaagt tgtcactga ctggagaact cggtttgtcg tctgttgcgg gggcggcagt       780 tatgcggtg ccgttgggca gtgcacccgt acctttggga gcgcgcgccc tcgtcgtgtc       840
gtgacgtcac ccgttctgtt ggcttataat gcagggtggg gccacctgcc ggtaggtgtg      900
cggtaggctt ttctccgtcg caggacgcag ggttcgggcc tagggtaggc tctcctgaat      960
cgacaggcgc cggacctctg gtgaggggag ggataagtga ggcgtcagtt tctttggtcg     1020
gttttatgta cctatcttct taagtagctg aagctccggt tttgaactat gcgctcgggg     1080
ttggcgagtg tgttttgtga agttttttag gcacctttg aaatgtaatc atttgggtca      1140
atatgtaatt ttcagtgtta gactagtaaa ttgtccgcta aattctggcc gttttggct      1200 tttttgttag acgaagcttg gtaccgagct cgatatcgcc accatggtga gcaagggcga     1260
ggagctgttc accggggtgg tgcccatcct ggtcgagctg gacggcgacg taaacggcca     1320
caagttcagc gtgtccggcg agggcgaggg cgatgccacc tacggcaagc tgaccctgaa     1380
gttcatctgc accaccggca agctgcccgt gccctggccc accctcgtga ccaccctgac     1440
ctacggcgtg cagtgcttca gccgctaccc cgaccacatg aagcagcacg acttcttcaa     1500
gtccgccatg cccgaaggct acgtccagga gcgcaccatc ttcttcaagg acgacggcaa     1560
ctacaagacc cgcgccgagg tgaagttcga gggcgacacc ctggtgaacc gcatcgagct     1620
gaagggcatc gacttcaagg aggacggcaa catcctgggg cacaagctgg agtacaacta     1680
caacagccac aacgtctata tcatggccga caagcagaag aacggcatca aggtgaactt     1740
caagatccgc cacaacatcg aggacggcag cgtgcagctc gccgaccact accagcagaa     1800
cacccccatc ggcgacggcc ccgtgctgct gcccgacaac cactacctga gcacccagtc     1860
cgccctgagc aaagacccca acgagaagcg cgatcacatg gtcctgctgg agttcgtgac     1920
cgccgccggg atcactctcg gcatggacga gctgtacaag ggcaatggcg gcaatgctag     1980
cagcggcgca cctccagcag attttccgtc cccacggaag agctctggag acagtggagg     2040
acccagcaca ccgtcagcat ctccactccc tgtagtcaca gaccacgcca tgacaaatga     2100
tgtcacctgg agcgaggcct cttcgcctga tgagaggaca ctcacctttg ctgaaagatg     2160
gcaattatct tcacctgatg gagtagatac agatgatgat ttaccaaaat cgcgagcatc     2220
caaaagaacc tgtggtgtga atgatgatga agtccaagc aaaattttta tggtgggaga     2280
atctccacaa gtgtcttcca gacttcagaa tttgagactg aataatttaa ttcccaggca     2340
acttttcaag cccaccgata atcaagaaac ttaggtcgac ccgggcggcc gcttcgagca     2400
gacatgataa gatacattga tgagtttgga caaaccacaa ctagaatgca gtgaaaaaaa     2460
```

```
tgctttattt gtgaaatttg tgatgctatt gctttatttg taaccattat aagctgcaat    2520
aaacaagtta acaacaacaa ttgcattcat tttatgtttc aggttcaggg ggagatgtgg    2580 gaggttttt  aaagcaagta aaacctctac aaatgtggta aaatccgata aggatcgatc    2640
cgggctggcg taatagcgaa gaggcccgca ccgatcgccc ttcccaacag ttgcgcagcc    2700
tgaatggcga atggacgcgc cctgtagcgg cgcattaagc gcggcgggtg tggtggttac    2760
gcgcagcgtg accgctacac ttgccagcgc cctagcgccc gctcctttcg ctttcttccc    2820
ttcctttctc gccacgttcg ccggctttcc ccgtcaagct ctaaatcggg gctcccttt    2880 agggttccga tttagtgctt tacggcacct cgaccccaaa aaacttgatt agggtgatgg    2940
ttcacgtagt gggccatcgc cctgatagac ggtttttcgc cctttgacgt tggagtccac    3000
gttctttaat agtggactct tgttccaaac tggaacaaca ctcaaccta  tctcggtcta    3060 ttcttttgat ttataaggga ttttgccgat ttcggcctat tggttaaaaa atgagctgat    3120
ttaacaaaaa tttaacgcga attttaacaa aatattaacg cttacaattt cctgatgcgg    3180
tattttctcc ttacgcatct gtgcggtatt tcacaccgca tacgcggatc tgcgcagcac    3240
catggcctga ataacctct  gaaagaggaa cttggttagg taccttctga ggcggaaaga    3300
accagctgtg gaatgtgtgt cagttagggt gtggaaagtc cccaggctcc ccagcaggca    3360
gaagtatgca aagcatgcat ctcaattagt cagcaaccag gtgtggaaag tccccaggct    3420
ccccagcagg cagaagtatg caaagcatgc atctcaatta gtcagcaacc atagtcccgc    3480
ccctaactcc gcccatcccg cccctaactc cgcccagttc cgcccattct ccgccccatg    3540
gctgactaat ttttttatt  tatgcagagg ccgaggccgc ctcggcctct gagctattcc    3600
agaagtagtg aggaggcttt tttggaggcc taggcttttg caaaaagctt gattcttctg    3660
acacaacagt ctcgaactta aggctagagc caccatgatt gaacaagatg gattgcacgc    3720
aggttctccg gccgcttggg tggagaggct attcggctat gactgggcac aacagacaat    3780
cggctgctct gatgccgccg tgttccggct gtcagcgcag gggcgcccgg ttcttttttgt    3840 caagaccgac ctgtccggtg ccctgaatga actgcaggac gaggcagcgc ggctatcgtg    3900
gctggccacg acgggcgttc cttgcgcagc tgtgctcgac gttgtcactg aagcgggaag    3960
ggactggctg ctattgggcg aagtgccggg gcaggatctc ctgtcatctc accttgctcc    4020
tgccgagaaa gtatccatca tggctgatgc aatgcggcgg ctgcatacgc ttgatccggc    4080
tacctgccca ttcgaccacc aagcgaaaca tcgcatcgag cgagcacgta ctcggatgga    4140
agccggtctt gtcgatcagg atgatctgga cgaagagcat caggggctcg cgccagccga    4200
actgttcgcc aggctcaagg cgcgcatgcc cgacggcgag gatctcgtcg tgacccatgg    4260
cgatgcctgc ttgccgaata tcatggtgga aaatggccgc ttttctggat tcatcgactg    4320
tggccggctg ggtgtggcgg accgctatca ggacatagcg ttggctaccc gtgatattgc    4380
tgaagagctt ggcggcgaat gggctgaccg cttcctcgtg ctttacggta tcgccgctcc    4440
cgattcgcag cgcatcgcct tctatcgcct tcttgacgag ttcttctgag cgggactctg    4500
gggttcgaaa tgaccgacca agcgacgccc aacctgccat cacgatggcc gcaataaaat    4560
atctttattt tcattacatc tgtgtgttgg ttttttgtgt gaatcgatag cgataaggat    4620
ccgcgtatgt tgcactctca gtacaatctg ctctgatgcc gcatagttaa gccagccccg    4680
acacccgcca acacccgctg acgcgccctg acgggcttgt ctgctcccgg catccgctta    4740
cagacaagct gtgaccgtct ccgggagctg catgtgtcag aggttttcac cgtcatcacc    4800
gaaacgcgcg agacgaaagg gcctcgtgat acgcctattt ttataggtta atgtcatgat    4860
```

| | |
|---|---|
| aataatggtt tcttagacgt caggtggcac ttttcgggga aatgtgcgcg gaacccctat | 4920 |
| ttgtttattt ttctaaatac attcaaatat gtatccgctc atgagacaat aaccctgata | 4980 |
| aatgcttcaa taatattgaa aaaggaagag tatgagtatt caacatttcc gtgtcgccct | 5040 |
| tattcccttt tttgcggcat tttgccttcc tgttttgct cacccagaaa cgctggtgaa | 5100 |
| agtaaaagat gctgaagatc agttgggtgc acgagtgggt tacatcgaac tggatctcaa | 5160 |
| cagcggtaag atccttgaga gttttcgccc cgaagaacgt tttccaatga tgagcacttt | 5220 |
| taaagttctg ctatgtggcg cggtattatc ccgtattgac gccgggcaag agcaactcgg | 5280 |
| tcgccgcata cactattctc agaatgactt ggttgagtac tcaccagtca cagaaaagca | 5340 |
| tcttacggat ggcatgacag taagagaatt atgcagtgct gccataacca tgagtgataa | 5400 |
| cactgcggcc aacttacttc tgacaacgat cggaggaccg aaggagctaa ccgcttttt | 5460 |
| gcacaacatg ggggatcatg taactcgcct tgatcgttgg gaaccggagc tgaatgaagc | 5520 |
| cataccaaac gacgagcgtg acaccacgat gcctgtagca atggcaacaa cgttgcgcaa | 5580 |
| actattaact ggcgaactac ttactctagc ttcccggcaa caattaatag actggatgga | 5640 |
| ggcggataaa gttgcaggac cacttctgcg ctcggccctt ccggctggct ggtttattgc | 5700 |
| tgataaatct ggagccggtg agcgtgggtc tcgcggtatc attgcagcac tggggccaga | 5760 |
| tggtaagccc tcccgtatcg tagttatcta cacgacgggg agtcaggcaa ctatggatga | 5820 |
| acgaaataga cagatcgctg agataggtgc ctcactgatt aagcattggt aactgtcaga | 5880 |
| ccaagtttac tcatatatac tttagattga tttaaaactt catttttaat ttaaaaggat | 5940 |
| ctaggtgaag atcctttttg ataatctcat gaccaaaatc ccttaacgtg agttttcgtt | 6000 |
| ccactgagcg tcagaccccg tagaaaagat caaaggatct tcttgagatc cttttttct | 6060 |
| gcgcgtaatc tgctgcttgc aaacaaaaaa accaccgcta ccagcggtgg tttgtttgcc | 6120 |
| ggatcaagag ctaccaactc tttttccgaa ggtaactggc ttcagcagag cgcagatacc | 6180 |
| aaatactgtt cttctagtgt agccgtagtt aggccaccac ttcaagaact ctgtagcacc | 6240 |
| gcctacatac ctcgctctgc taatcctgtt accagtggct gctgccagtg gcgataagtc | 6300 |
| gtgtcttacc gggttggact caagacgata gttaccggat aaggcgcagc ggtcgggctg | 6360 |
| aacggggggt tcgtgcacac agcccagctt ggagcgaacg acctacaccg aactgagata | 6420 |
| cctacagcgt gagctatgag aaagcgccac gcttcccgaa gggagaaagg cggacaggta | 6480 |
| tccggtaagc ggcagggtcg gaacaggaga gcgcacgagg gagcttccag ggggaaacgc | 6540 |
| ctggtatctt tatagtcctg tcgggtttcg ccacctctga cttgagcgtc gatttttgtg | 6600 |
| atgctcgtca gggggggcgga gcctatggaa aaacgccagc aacgcggcct ttttacggtt | 6660 |
| cctggccttt tgctggcctt ttgctcacat ggctcgacag atct | 6704 |

<210> SEQ ID NO 4
<211> LENGTH: 9937
<212> TYPE: DNA
<213> ORGANISM: Artificial Sequence
<220> FEATURE:
<223> OTHER INFORMATION: pCORON1002-EGFP-C1-BGAL-PSLD

<400> SEQUENCE: 4

| | |
|---|---|
| ggcctccgcg ccgggttttg gcgcctcccg cgggcgcccc cctcctcacg gcgagcgctg | 60 |
| ccacgtcaga cgaagggcgc agcgagcgtc ctgatccttc cgcccggacg ctcaggacag | 120 |
| cggcccgctg ctcataagac tcggccttag aaccccagta tcagcagaag gacattttag | 180 |

| | |
|---|---:|
| gacgggactt gggtgactct agggcactgg ttttctttcc agagagcgga acaggcgagg | 240 |
| aaaagtagtc ccttctcggc gattctgcgg agggatctcc gtgggcggt gaacgccgat | 300 |
| gattatataa ggacgcgccg ggtgtggcac agctagttcc gtcgcagccg ggatttgggt | 360 |
| cgcggttctt gtttgtggat cgctgtgatc gtcacttggt gagtagcggg ctgctgggct | 420 |
| ggccggggct ttcgtggccg ccgggccgct cggtgggacg gaagcgtgtg gagagaccgc | 480 |
| caagggctgt agtctgggtc cgcgagcaag gttgccctga actgggggtt gggggagcg | 540 |
| cagcaaaatg gcggctgttc ccgagtcttg aatggaagac gcttgtgagg cgggctgtga | 600 |
| ggtcgttgaa acaaggtggg gggcatggtg ggcggcaaga acccaaggtc ttgaggcctt | 660 |
| cgctaatgcg ggaaagctct tattcgggtg agatgggctg ggcaccatc tggggaccct | 720 |
| gacgtgaagt ttgtcactga ctggagaact cggtttgtcg tctgttgcgg gggcggcagt | 780 |
| tatggcggtg ccgttgggca gtgcacccgt acctttggga gcgcgcgccc tcgtcgtgtc | 840 |
| gtgacgtcac ccgttctgtt ggcttataat gcagggtggg gccacctgcc ggtaggtgtg | 900 |
| cggtaggctt ttctccgtcg caggacgcag ggttcgggcc tagggtaggc tctcctgaat | 960 |
| cgacaggcgc cggacctctg gtgaggggag ggataagtga ggcgtcagtt tctttggtcg | 1020 |
| gttttatgta cctatcttct taagtagctg aagctccggt tttgaactat gcgctcgggg | 1080 |
| ttggcgagtg tgttttgtga agttttttag gcacctttg aaatgtaatc atttgggtca | 1140 |
| atatgtaatt ttcagtgtta gactagtaaa ttgtccgcta aattctggcc gttttggct | 1200 |
| tttttgttag acgaagcttg gtaccgagct cgatatcgct agcgctaccg gtcgccacca | 1260 |
| tggtgagcaa gggcgaggag ctgttcaccg gggtggtgcc catcctggtc gagctggacg | 1320 |
| gcgacgtaaa cggccacaag ttcagcgtgt ccggcgaggg cgaggcgat gccacctacg | 1380 |
| gcaagctgac cctgaagttc atctgcacca ccggcaagct gcccgtgccc tggcccaccc | 1440 |
| tcgtgaccac cctgacctac ggcgtgcagt gcttcagccg ctaccccgac cacatgaagc | 1500 |
| agcacgactt cttcaagtcc gccatgcccg aaggctacgt ccaggagcgc accatcttct | 1560 |
| tcaaggacga cggcaactac aagacccgcg ccgaggtgaa gttcgagggc gacaccctgg | 1620 |
| tgaaccgcat cgagctgaag ggcatcgact tcaaggagga cggcaacatc ctggggcaca | 1680 |
| agctggagta caactacaac agccacaacg tctatatcat ggccgacaag cagaagaacg | 1740 |
| gcatcaaggt gaacttcaag atccgccaca acatcgagga cggcagcgtg cagctcgccg | 1800 |
| accactacca gcagaacacc cccatcggcg acggccccgt gctgctgccc gacaaccact | 1860 |
| acctgagcac ccagtccgcc ctgagcaaag accccaacga gaagcgcgat cacatggtcc | 1920 |
| tgctggagtt cgtgaccgcc gccgggatca ctctcggcat ggacgagctg tacaagtccg | 1980 |
| gactcagatc tcgagctcaa gcttccatgt cgtttacttt gaccaacaag aacgtgattt | 2040 |
| tcgttgccgg tctgggaggc attggtctgg acaccagcaa ggagctgctc aagcgcgatc | 2100 |
| ccgtcgtttt acaacgtcgt gactgggaaa accctgcgt tacccaactt aatcgccttg | 2160 |
| cagcacatcc cccttttcgcc agctggcgta atagcgaaga ggcccgcacc gatcgccctt | 2220 |
| cccaacagtt gcgcagcctg aatggcgaat ggcgctttgc ctggtttccg gcaccagaag | 2280 |
| cggtgccgga agctggctg gagtgcgatc ttcctgaggc cgatactgtc gtcgtccct | 2340 |
| caaactggca gatgcacggt tacgatgcgc ccatctacac caacgtgacc tatcccatta | 2400 |
| cggtcaatcc gccgtttgtt cccacggaga atccgacggg ttgttactcg ctcacattta | 2460 |
| atgttgatga agctggcta caggaaggcc agacgcgaat tatttttgat ggcgttaact | 2520 |
| cggcgtttca tctgtggtgc aacgggcgct gggtcggtta cggccaggac agtcgtttgc | 2580 |

```
cgtctgaatt tgacctgagc gcattttac  gcgccggaga aaaccgcctc gcggtgatgg   2640
tgctgcgttg gagtgacggc agttatctgg aagatcagga tatgtggcgg atgagcggca   2700
ttttccgtga cgtctcgttg ctgcataaac cgactacaca aatcagcgat ttccatgttg   2760
ccactcgctt taatgatgat ttcagccgcg ctgtactgga ggctgaagtt cagatgtgcg   2820
gcgagttgcg tgactaccta cgggtaacag tttctttatg gcagggtgaa acgcaggtcg   2880
ccagcggcac cgcgcctttc ggcggtgaaa ttatcgatga gcgtggtggt tatgccgatc   2940
gcgtcacact acgtctgaac gtcgaaaacc cgaaactgtg gagcgccgaa atcccgaatc   3000
tctatcgtgc ggtggttgaa ctgcacaccg ccgacggcac gctgattgaa gcagaagcct   3060
gcgatgtcgg tttccgcgag gtgcggattg aaaatggtct gctgctgctg aacggcaagc   3120
cgttgctgat tcgaggcgtt aaccgtcacg agcatcatcc tctgcatggt caggtcatgg   3180
atgagcagac gatggtgcag gatatcctgc tgatgaagca gaacaacttt aacgccgtgc   3240
gctgttcgca ttatccgaac catccgctgt ggtacacgct gtgcgaccgc tacggcctgt   3300
atgtggtgga tgaagccaat attgaaaccc acggcatggt gccaatgaat cgtctgaccg   3360
atgatccgcg ctggctaccg gcgatgagcg aacgcgtaac gcgaatggtg cagcgcgatc   3420
gtaatcaccc gagtgtgatc atctggtcgc tggggaatga atcaggccac ggcgctaatc   3480
acgacgcgct gtatcgctgg atcaaatctg tcgatccttc ccgcccggtg cagtatgaag   3540 gcggcgagc cgacaccacg gccaccgata ttatttgccc gatgtacgcg cgcgtggatg    3600
aagaccagcc cttcccggct gtgccgaaat ggtccatcaa aaaatggctt tcgctacctg   3660
gagagacgcg cccgctgatc ctttgcgaat acgcccacgc gatgggtaac agtcttggcg   3720
gtttcgctaa atactggcag gcgtttcgtc agtatcccg  tttacagggc ggcttcgtct   3780
gggactgggt ggatcagtcg ctgattaaat atgatgaaaa cggcaacccg tggtcggctt   3840
acggcggtga ttttggcgat acgccgaacg atcgccagtt ctgtatgaac ggtctggtct   3900
ttgccgaccg cacgccgcat ccagcgctga cggaagcaaa acaccagcag cagttttttcc  3960 agttccgttt atccgggcaa accatcgaag tgaccagcga ataccctgttc cgtcatagcg   4020 ataacgagct cctgcactgg atggtggcgc tggatggtaa ccgctggca  agcggtgaag   4080 tgcctctgga tgtcgctcca caaggtaaac agttgattga actgcctgaa ctaccgcagc   4140
cggagagcgc cgggcaactc tggctcacag tacgcgtagt gcaaccgaac gcgaccgcat   4200
ggtcagaagc cgggcacatc agcgcctggc agcagtggcg tctggcggaa aacctcagtg   4260
tgacgctccc cgccgcgtcc cacgccatcc gcatctgac  caccagcgaa atggattttt   4320
gcatcgagct gggtaataag cgttggcaat ttaaccgcca gtcaggcttt ctttcacaga   4380
tgtggattgg cgataaaaaa caactgctga cgccgctgcg cgatcagttc acccgtgcac   4440
cgctggataa cgacattggc gtaagtgaag cgacccgcat tgaccctaac gcctgggtcg   4500
aacgctggaa ggcggcgggc cattaccagg ccgaagcagc gttgttgcag tgcacggcag   4560
atacacttgc tgatgcggtg ctgattacga ccgctcacgc gtggcagcat caggggaaaa   4620
ccttatttat cagccggaaa acctaccgga ttgatggtag tggtcaaatg gcgattaccg   4680
ttgatgttga agtggcgagc gataccaccgc atccggcgcg gattggcctg aactgccagc   4740
tggcgcaggt agcagagcgg gtaaactggc tcggattagg gccgcaagaa aactatcccg   4800
accgccttac tgccgcctgt tttgaccgct gggatctgcc attgtcagac atgtataccc   4860
cgtacgtctt cccgagcgaa aacggtctgc gctgcgggac gcgcgaattg aattatggcc   4920
```

```
cacaccagtg gcgcggcgac ttccagttca acatcagccg ctacagtcaa cagcaactga   4980
tggaaaccag ccatcgccat tgctgcacg gggaagaagg cacatggctg aatatcgacg    5040
gtttccatat ggggattggt ggcgacgact cctggagccc gtcagtatcg gcggaattac   5100
agctgagatc tagcggcgca cctccagcag attttccgtc cccacggaag agctctggag   5160
acagtggagg acccagcaca ccgtcagcat ctccactccc tgtagtcaca gaccacgcca   5220
tgacaaatga tgtcacctgg agcgaggcct cttcgcctga tgagaggaca ctcacctttg   5280
ctgaaagatg gcaattatct tcacctgatg gagtagatac agatgatgat ttaccaaaat   5340
cgcgagcatc caaaagaacc tgtggtgtga atgatgatga aagtccaagc aaaattttta   5400
tggtgggaga atctccacaa gtgtcttcca gacttcagaa tttgagactg aataatttaa   5460
ttcccaggca acttttcaag cccaccgata atcaagaaac ttagttttat ttcaaattgt   5520
tccgagtaac tatgttttc tattggagac aaaatgaaca tcgtaacgtc aaagtaccaa    5580
gataagaatt ctgcagtcga cggtaccgcg ggcccgggcg gccgcttcga gcagacatga   5640
taagatacat tgatgagttt ggacaaacca aactagaat gcagtgaaaa aaatgcttta    5700
tttgtgaaat ttgtgatgct attgctttat ttgtaaccat tataagctgc aataaacaag   5760
ttaacaacaa caattgcatt cattttatgt ttcaggttca gggggagatg tgggaggttt   5820
tttaaagcaa gtaaaacctc tacaaatgtg gtaaaatccg ataaggatcg atccgggctg   5880
gcgtaatagc gaagaggccc gcaccgatcg cccttcccaa cagttgcgca gcctgaatgg   5940
cgaatggacg cgcctgtag cggcgcatta agcgcggcgg gtgtggtggt tacgcgcagc    6000
gtgaccgcta cacttgccag cgccctagcg cccgctcctt tcgctttctt cccttccttt   6060
ctcgccacgt tcgccggctt tccccgtcaa gctctaaatc ggggctccc tttaggttc     6120 cgatttagtg ctttacggca cctcgacccc aaaaaacttg attagggtga tggttcacgt   6180
agtgggccat cgccctgata gacggttttt cgccctttga cgttggagtc cacgttcttt   6240
aatagtggac tcttgttcca aactggaaca acactcaacc ctatctcggt ctattctttt   6300
gatttataag ggatttttgcc gatttcggcc tattggttaa aaaatgagct gatttaacaa   6360
aaatttaacg cgaattttaa caaaatatta acgcttacaa ttttcctgatg cggtattttc   6420 tccttacgca tctgtgcggt atttcacacc gcatacgcgg atctgcgcag caccatggcc   6480
tgaaataacc tctgaaagag gaacttggtt aggtaccttc tgaggcggaa agaaccagct   6540
gtggaatgtg tgtcagttag ggtgtggaaa gtccccaggc tccccagcag gcagaagtat   6600
gcaaagcatg catctcaatt agtcagcaac caggtgtgga aagtccccag gctccccagc   6660
aggcagaagt atgcaaagca tgcatctcaa ttagtcagca accatagtcc cgcccctaac   6720
tccgcccatc ccgcccctaa ctccgcccag ttccgcccat tctccgcccc atggctgact   6780 aattttttt atttatgcag aggccgaggc cgcctcggcc tctgagctat tccagaagta   6840
gtgaggaggc ttttttggag gcctaggctt ttgcaaaaag cttgattctt ctgacacaac   6900
agtctcgaac ttaaggctag agccaccatg attgaacaag atggattgca cgcaggttct   6960
ccggccgctt gggtggagag gctattcggc tatgactggg cacaacagac aatcggctgc   7020
tctgatgccg ccgtgttccg gctgtcagcg caggggcgcc cggttctttt tgtcaagacc   7080
gacctgtccg gtgccctgaa tgaactgcag gacgaggcag cgcggctatc gtggctggcc   7140
acgacgggcg ttccttgcgc agctgtgctc gacgttgtca ctgaagcggg aagggactgg   7200
ctgctattgg gcgaagtgcc ggggcaggat ctcctgtcat ctcaccttgc tcctgccgag   7260
aaagtatcca tcatggctga tgcaatgcgg cggctgcata cgcttgatcc ggctacctgc   7320
```

```
ccattcgacc accaagcgaa acatcgcatc gagcgagcac gtactcggat ggaagccggt   7380
cttgtcgatc aggatgatct ggacgaagag catcaggggc tcgcgccagc cgaactgttc   7440
gccaggctca aggcgcgcat gcccgacggc gaggatctcg tcgtgaccca tggcgatgcc   7500
tgcttgccga atatcatggt ggaaaatggc cgcttttctg gattcatcga ctgtggccgg   7560
ctgggtgtgg cggaccgcta tcaggacata gcgttggcta cccgtgatat tgctgaagag   7620
cttggcggcg aatgggctga ccgcttcctc gtgctttacg gtatcgccgc tcccgattcg   7680
cagcgcatcg ccttctatcg ccttcttgac gagttcttct gagcgggact ctggggttcg   7740
aaatgaccga ccaagcgacg cccaacctgc catcacgatg gccgcaataa aatatcttta   7800
ttttcattac atctgtgtgt tggttttttg tgtgaatcga tagcgataag gatccgcgta   7860
tggtgcactc tcagtacaat ctgctctgat gccgcatagt taagccagcc ccgacacccg   7920
ccaacacccg ctgacgcgcc ctgacgggct tgtctgctcc cggcatccgc ttacagacaa   7980
gctgtgaccg tctccgggag ctgcatgtgt cagaggtttt caccgtcatc accgaaacgc   8040
gcgagacgaa agggcctcgt gatacgccta tttttatagg ttaatgtcat gataataatg   8100
gtttcttaga cgtcaggtgg cacttttcgg ggaaatgtgc gcggaacccc tatttgttta   8160
tttttctaaa tacattcaaa tatgtatccg ctcatgagac aataaccctg ataaatgctt   8220
caataatatt gaaaaaggaa gagtatgagt attcaacatt tccgtgtcgc ccttattccc   8280
ttttttgcgg cattttgcct tcctgttttt gctcacccag aaacgctggt gaaagtaaaa   8340
gatgctgaag atcagttggg tgcacgagtg ggttacatcg aactggatct caacagcggt   8400
aagatccttg agagttttcg ccccgaagaa cgttttccaa tgatgagcac ttttaaagtt   8460
ctgctatgtg gcgcggtatt atcccgtatt gacgccgggc aagagcaact cggtcgccgc   8520
atacactatt ctcagaatga cttggttgag tactcaccag tcacagaaaa gcatcttacg   8580
gatggcatga cagtaagaga attatgcagt gctgccataa ccatgagtga taacactgcg   8640
gccaacttac ttctgacaac gatcggagga ccgaaggagc taaccgcttt tttgcacaac   8700
atgggggatc atgtaactcg ccttgatcgt tgggaaccgg agctgaatga agccatacca   8760
aacgacgagc gtgacaccac gatgcctgta gcaatggcaa caacgttgcg caaactatta   8820
actggcgaac tacttactct agcttcccgg caacaattaa tagactggat ggaggcggat   8880
aaagttgcag gaccacttct gcgctcggcc cttccggctg gctggtttat tgctgataaa   8940
tctggagccg gtgagcgtgg gtctcgcggt atcattgcag cactggggcc agatggtaag   9000
ccctcccgta tcgtagttat ctacacgacg gggagtcagg caactatgga tgaacgaaat   9060
agacagatcg ctgagatagg tgcctcactg attaagcatt ggtaactgtc agaccaagtt   9120
tactcatata ctttagat tgatttaaaa cttcatttt aatttaaaag gatctaggtg   9180
aagatccttt ttgataatct catgaccaaa atcccttaac gtgagttttc gttccactga   9240
gcgtcagacc ccgtagaaaa gatcaaagga tcttcttgag atcctttttt tctgcgcgta   9300
atctgctgct tgcaaacaaa aaaaccaccg ctaccagcgg tggtttgttt gccggatcaa   9360
gagctaccaa ctctttttcc gaaggtaact ggcttcagca gagcgcagat accaaatact   9420
gttcttctag tgtagccgta gttaggccac cacttcaaga actctgtagc accgcctaca   9480
tacctcgctc tgctaatcct gttaccagtg gctgctgcca gtggcgataa gtcgtgtctt   9540
accgggttgg actcaagacg atagttaccg gataaggcgc agcggtcggg ctgaacgggg   9600
ggttcgtgca cacagcccag cttggagcga acgacctaca ccgaactgag atacctacag   9660
```

-continued

```
cgtgagctat gagaaagcgc cacgcttccc gaagggagaa aggcggacag gtatccggta      9720
agcggcaggg tcggaacagg agagcgcacg agggagcttc caggggggaaa cgcctggtat     9780 ctttatagtc ctgtcgggtt tcgccacctc tgacttgagc gtcgattttt gtgatgctcg     9840
tcaggggggc ggagcctatg gaaaaacgcc agcaacgcgg ccttttttacg gttcctggcc    9900 ttttgctggc cttttgctca catggctcga cagatct                              9937
```

<210> SEQ ID NO 5
<211> LENGTH: 376
<212> TYPE: PRT
<213> ORGANISM: Artificial Sequence
<220> FEATURE:
<223> OTHER INFORMATION: EGFP-PSLD fusion protein

<400> SEQUENCE: 5

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Gly
225                 230                 235                 240

Asn Gly Gly Asn Ala Ser Ser Gly Ala Pro Ala Asp Phe Pro Ser
                245                 250                 255

Pro Arg Lys Ser Ser Gly Asp Ser Gly Gly Pro Ser Thr Pro Ser Ala
            260                 265                 270

Ser Pro Leu Pro Val Val Thr Asp His Ala Met Thr Asn Asp Val Thr
        275                 280                 285

Trp Ser Glu Ala Ser Ser Pro Asp Glu Arg Thr Leu Thr Phe Ala Glu
290                 295                 300

Arg Trp Gln Leu Ser Ser Pro Asp Gly Val Asp Thr Asp Asp Leu
305                 310                 315                 320
```

```
Pro Lys Ser Arg Ala Ser Lys Arg Thr Cys Gly Val Asn Asp Asp Glu
            325                 330                 335

Ser Pro Ser Lys Ile Phe Met Val Gly Glu Ser Pro Gln Val Ser Ser
        340                 345                 350

Arg Leu Gln Asn Leu Arg Leu Asn Asn Leu Ile Pro Arg Gln Leu Phe
            355                 360                 365

Lys Pro Thr Asp Asn Gln Glu Thr
        370                 375

<210> SEQ ID NO 6
<211> LENGTH: 1128
<212> TYPE: DNA
<213> ORGANISM: Artificial Sequence
<220> FEATURE:
<223> OTHER INFORMATION: EGFP-PSLD nucleic acid

<400> SEQUENCE: 6
atggtgagca agggcgagga gctgttcacc ggggtggtgc ccatcctggt cgagctggac     60
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccctgaccta cggcgtgcag tgcttcagcc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaagggc    720
aatggcggca tgctagcagc ggcgcacct ccagcagatt ttccgtcccc acggaagagc    780
tctggagaca gtggaggacc cagcacaccg tcagcatctc cactccctgt agtcacagac    840
cacgccatga caaatgatgt cacctggagc gaggcctctt cgcctgatga aggacactc    900 acctttgctg aaagatggca attatcttca cctgatggag tagatacaga tgatgattta    960
ccaaaatcgc gagcatccaa agaacctgt ggtgtgaatg atgatgaaag tccaagcaaa   1020
atttttatgg tgggagaatc tccacaagtg tcttccagac ttcagaattt gagactgaat   1080
aatttaattc ccaggcaact tttcaagccc accgataatc aagaaact                1128

<210> SEQ ID NO 7
<211> LENGTH: 22
<212> TYPE: PRT
<213> ORGANISM: Human immunodeficiency virus

<400> SEQUENCE: 7

Ala Glu Pro Val Pro Leu Gln Leu Pro Pro Leu Glu Arg Leu Thr Leu
1               5                   10                  15

Asp Cys Ser Glu Asp Cys
            20

<210> SEQ ID NO 8
<211> LENGTH: 19
<212> TYPE: PRT
```

<213> ORGANISM: Homo sapiens

<400> SEQUENCE: 8

Gln Leu Val Glu Glu Leu Leu Lys Ile Ile Cys Ala Phe Gln Leu Asp
1               5                   10                  15

Thr Gly Leu

<210> SEQ ID NO 9
<211> LENGTH: 22
<212> TYPE: PRT
<213> ORGANISM: Homo sapiens

<400> SEQUENCE: 9

Gly Arg Pro Ser Thr Arg Ile Gln Gln Gln Leu Gly Gln Leu Thr Leu
1               5                   10                  15

Asp Cys Ser Glu Asp Cys
            20

<210> SEQ ID NO 10
<211> LENGTH: 22
<212> TYPE: PRT
<213> ORGANISM: Homo sapiens

<400> SEQUENCE: 10

Glu Thr Asn Leu Glu Ala Leu Gln Lys Lys Leu Glu Glu Leu Glu Leu
1               5                   10                  15

Asp Glu Gln Gln Arg Lys
            20

<210> SEQ ID NO 11
<211> LENGTH: 22
<212> TYPE: PRT
<213> ORGANISM: Homo sapiens

<400> SEQUENCE: 11

Ser Gly Asn Ser Asn Glu Leu Ala Leu Lys Leu Ala Gly Leu Asp Ile
1               5                   10                  15

Asn Lys Thr Glu Gly Glu
            20

<210> SEQ ID NO 12
<211> LENGTH: 12
<212> TYPE: PRT
<213> ORGANISM: Homo sapiens

<400> SEQUENCE: 12

Lys Val Ala Glu Lys Leu Glu Ala Leu Ser Val Arg
1               5                   10

<210> SEQ ID NO 13
<211> LENGTH: 22
<212> TYPE: PRT
<213> ORGANISM: Homo sapiens

<400> SEQUENCE: 13

Arg Glu Arg Phe Glu Met Phe Arg Glu Leu Asn Glu Ala Leu Glu Leu
1               5                   10                  15

Lys Asp Ala Gln Ala Gly
            20

<210> SEQ ID NO 14
<211> LENGTH: 22

```
<212> TYPE: PRT
<213> ORGANISM: Homo sapiens

<400> SEQUENCE: 14

Lys Asp Ser Thr Leu Ile Met Gln Leu Leu Arg Asp Asn Leu Thr Leu
1               5                   10                  15

Trp Thr Ser Asp Thr Gln
            20

<210> SEQ ID NO 15
<211> LENGTH: 18
<212> TYPE: PRT
<213> ORGANISM: Homo sapiens

<400> SEQUENCE: 15

Ser Asp Ser Ile Ser Leu Ser Phe Asp Glu Ser Leu Ala Leu Cys Val
1               5                   10                  15

Ile Arg

<210> SEQ ID NO 16
<211> LENGTH: 24
<212> TYPE: PRT
<213> ORGANISM: Mus musculus

<400> SEQUENCE: 16

Glu Ala Pro Ser Pro Gln Val Ser Ser Val Phe Gln Asn Met Arg Leu
1               5                   10                  15

Asn Thr Leu Thr Pro Arg Gln Leu
            20

<210> SEQ ID NO 17
<211> LENGTH: 24
<212> TYPE: PRT
<213> ORGANISM: Homo sapiens

<400> SEQUENCE: 17

Val Gly Glu Ser Pro Gln Val Ser Ser Arg Leu Gln Asn Leu Arg Leu
1               5                   10                  15

Asn Asn Leu Ile Pro Arg Gln Leu
            20

<210> SEQ ID NO 18
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 18

Gly Asn Gly Gly Asn Ala Ser
1               5
```